US011635437B2

(12) United States Patent
Tsay et al.

(10) Patent No.: US 11,635,437 B2
(45) Date of Patent: Apr. 25, 2023

(54) METHOD FOR VERIFYING THE PRIMARY STRUCTURE OF PROTEIN

(71) Applicant: Sun Jet Biotechnology Inc., Taipei (TW)

(72) Inventors: Yeou Guang Tsay, Taipei (TW); Ya-Fen Chen, Taipei (TW)

(73) Assignee: SUN JET BIOTECHNOLOGY INC., Taipei (TW)

( * ) Notice: Subject to any disclaimer, the term of this patent is extended or adjusted under 35 U.S.C. 154(b) by 1340 days.

(21) Appl. No.: 15/778,534

(22) PCT Filed: Nov. 23, 2016

(86) PCT No.: PCT/CN2016/106962
§ 371 (c)(1),
(2) Date: May 23, 2018

(87) PCT Pub. No.: WO2017/088769
PCT Pub. Date: Jun. 1, 2017

(65) Prior Publication Data
US 2018/0356425 A1    Dec. 13, 2018

Related U.S. Application Data

(60) Provisional application No. 62/259,031, filed on Nov. 23, 2015.

(51) Int. Cl.
*G01N 33/68*    (2006.01)
*G16B 15/00*    (2019.01)
(Continued)

(52) U.S. Cl.
CPC ..... *G01N 33/6848* (2013.01); *G01N 33/6851* (2013.01); *G16B 15/00* (2019.02); *G16B 40/00* (2019.02); *G16B 40/10* (2019.02); *H01J 49/0036* (2013.01); *G01N 2440/38* (2013.01); *G01N 2560/00* (2013.01); *G01N 2570/00* (2013.01)

(58) Field of Classification Search
None
See application file for complete search history.

(56) References Cited

U.S. PATENT DOCUMENTS

2011/0282587 A1*   11/2011   Jones ...................... G06F 17/10
702/22

FOREIGN PATENT DOCUMENTS

WO    WO-2004081535 A2 *   9/2004   ......... G01N 33/6803

* cited by examiner

*Primary Examiner* — Jennifer Wecker
*Assistant Examiner* — Bryan Kilpatrick
(74) *Attorney, Agent, or Firm* — Birch, Stewart, Kolasch & Birch, LLP

(57) ABSTRACT

Disclosed herein is a method for verifying the primary structure of a protein through comparative analyses between ion clusters observed in mass spectra and a series of simulated ion clusters deduced from its putative chemical formula. The method comprises the steps of: preparing a protein sample for mass spectrometric analyses; collecting mass spectra of the protein sample; obtaining master ion cluster from a plurality of ion clusters in the mass spectra; producing a series of simulated ion clusters according to the chemical formula of the protein; finding the best fit for the master ion cluster among the series of simulated ion clusters; and verifying if said best-fit simulated ion cluster corresponds to the chemical formula of the protein.

22 Claims, 19 Drawing Sheets

(51) Int. Cl.
*G16B 40/00* (2019.01)
*H01J 49/00* (2006.01)
*G16B 40/10* (2019.01)

(A)

Human erythropoietin ($C_{834}H_{1338}O_{261}N_{228}S_5$)

```
APPRLICDSR  VLERYLLEAK  EAEDITTGCA  EHCSLNEDIT
                        N→D         N→D

VPDTKVNFYA  WKRMEVGQQA  VEVWQGLALL  SEAVLRGQAL

LVDSSQPWEP  LQLHVDKAVS  GLRSLTTLLR  ALGAQKEAIS
N→D

PPDAASAAPL  RTITADTFRK  LFRVYSNFLR  GKLKLYTGEA
     +NeuAc-Hex-HexNAc

CRTGD
```

(B)

Human erythropoietin ($C_{835}H_{1355}O_{269}N_{229}S_5$)

```
APPRLICDSR  VLERYLLEAK  EAEDITTGCA  EHCSLNEDIT
                        N→D         N→D

VPDTKVNFYA  WKRMEVGQQA  VEVWQGLALL  SEAVLRGQAL

LVDSSQPWEP  LQLHVDKAVS  GLRSLTTLLR  ALGAQKEAIS
N→D

PPDAASAAPL  RTITADTFRK  LFRVYSNFLR  GKLKLYTGEA
     +NeuAc-Hex-HexNAc-NeuAc

CRTGD
```

Figure 2

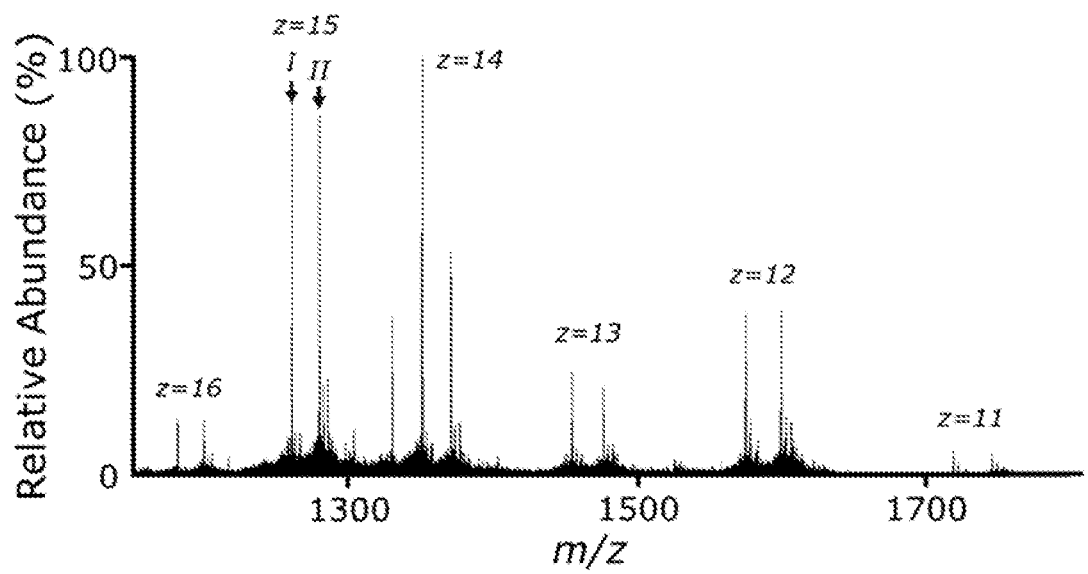
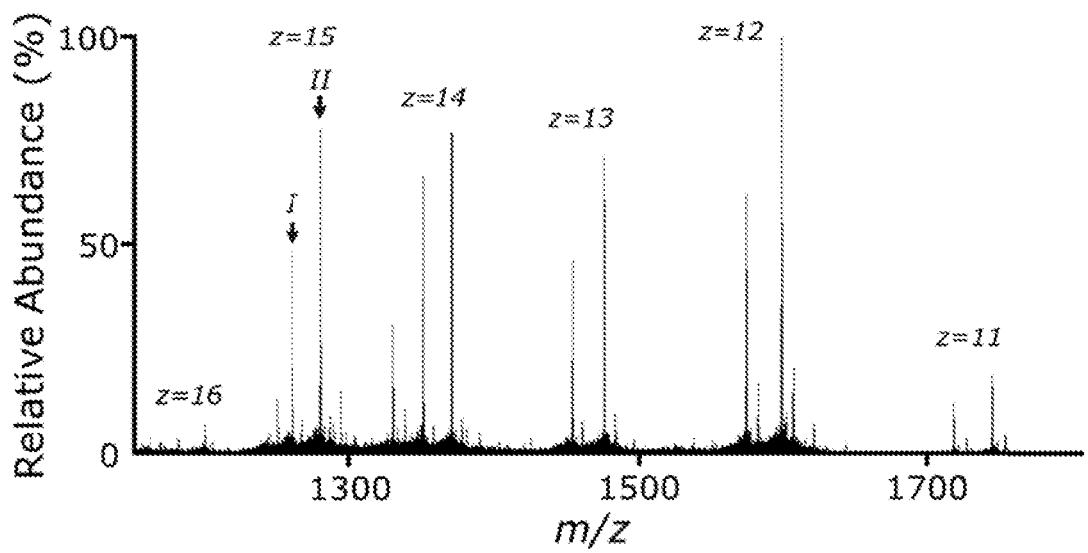
Figure 4

|  | 0 | 1 | 2 | (n-1) | n |
|---|---|---|---|---|---|
| $C_{v-1}$ | $I_{0,v-1}$ | $I_{1,v-1}$ | $I_{2,v-1}$ | $I_{n-1,v-1}$ | $I_{n,v-1}$ |
| $C_v$ | $I_{0,v}$ | $I_{1,v}$ | $I_{2,v}$ | +13C | $I_{n,v}$ |

$$I_{n,v} = A_{12C} \cdot I_{n,v-1} + A_{13C} \cdot I_{n-1,v-1}$$

+12C

|  | 0 | 1 | 2 | (n-1) | n |
|---|---|---|---|---|---|
| $H_{w-1}$ | $I_{0,w-1}$ | $I_{1,w-1}$ | $I_{2,w-1}$ | $I_{n-1,w-1}$ | $I_{n,w-1}$ |
| $H_w$ | $I_{0,w}$ | $I_{1,w}$ | $I_{2,w}$ | +2H | $I_{n,w}$ |

$$I_{n,w} = A_{1H} \cdot I_{n,w-1} + A_{2H} \cdot I_{n-1,w-1}$$

+1H

|  | 0 | 1 | 2 | (n-1) | n |
|---|---|---|---|---|---|
| $N_{y-1}$ | $I_{0,y-1}$ | $I_{1,y-1}$ | $I_{2,y-1}$ | $I_{n-1,y-1}$ | $I_{n,y-1}$ |
| $N_y$ | $I_{0,y}$ | $I_{1,y}$ | $I_{2,y}$ | +15N | $I_{n,y}$ |

$$I_{n,y} = A_{14N} \cdot I_{n,y-1} + A_{15N} \cdot I_{n-1,y-1}$$

|  | 0 | 1 | 2 | (n-2) | (n-1) | n |
|---|---|---|---|---|---|---|
| $O_{x-1}$ | $I_{0,x-1}$ | $I_{1,x-1}$ | $I_{2,x-1}$ | $I_{n-2,x-1}$ | $I_{n-1,x-1}$ | $I_{n,x-1}$ |
| $O_x$ | $I_{0,x}$ | $I_{1,x}$ | $I_{2,x}$ | +18O | +17O | $I_{n,x}$ |

$$I_{n,x} = A_{16O} \cdot I_{n,x-1} + A_{17O} \cdot I_{n-1,x-1} + A_{18O} \cdot I_{n-2,x-1}$$

|  | 0 | 1 | (n-4) | (n-3) | (n-2) | (n-1) | n |
|---|---|---|---|---|---|---|---|
| $S_{z-1}$ | $I_{0,z-1}$ | $I_{1,z-1}$ | $I_{n-4,z-1}$ | $I_{n-3,z-1}$ | $I_{n-2,z-1}$ | $I_{n-1,z-1}$ | $I_{n,z-1}$ |
| $S_z$ | $I_{0,z}$ | $I_{1,z}$ | +36S | | +34S | +33S | $I_{n,z}$ |

$$I_{n,z} = A_{32S} \cdot I_{n,z-1} + A_{33S} \cdot I_{n-1,z-1} + A_{34S} \cdot I_{n-2,z-1} + A_{36S} \cdot I_{n-4,z-1}$$

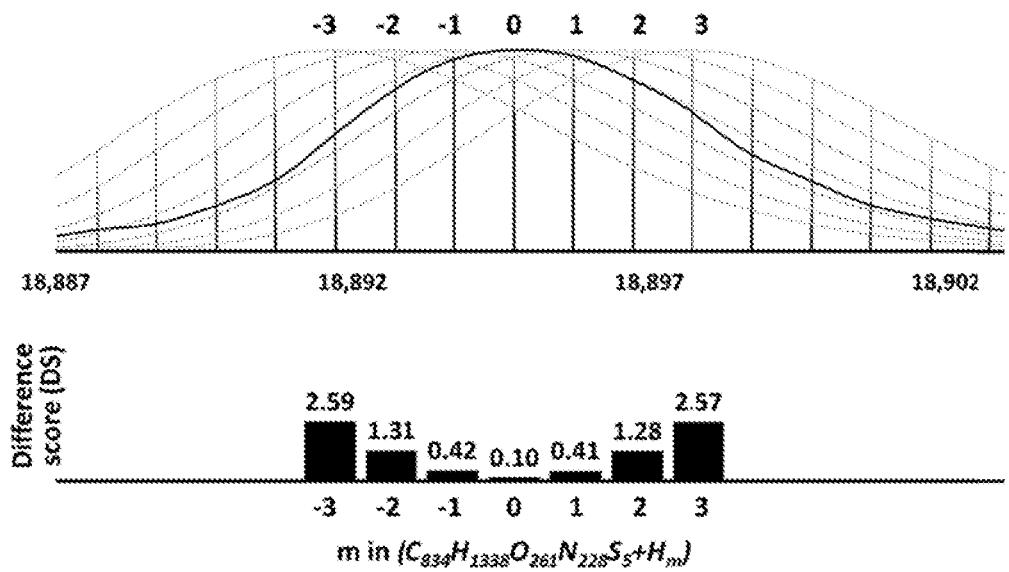
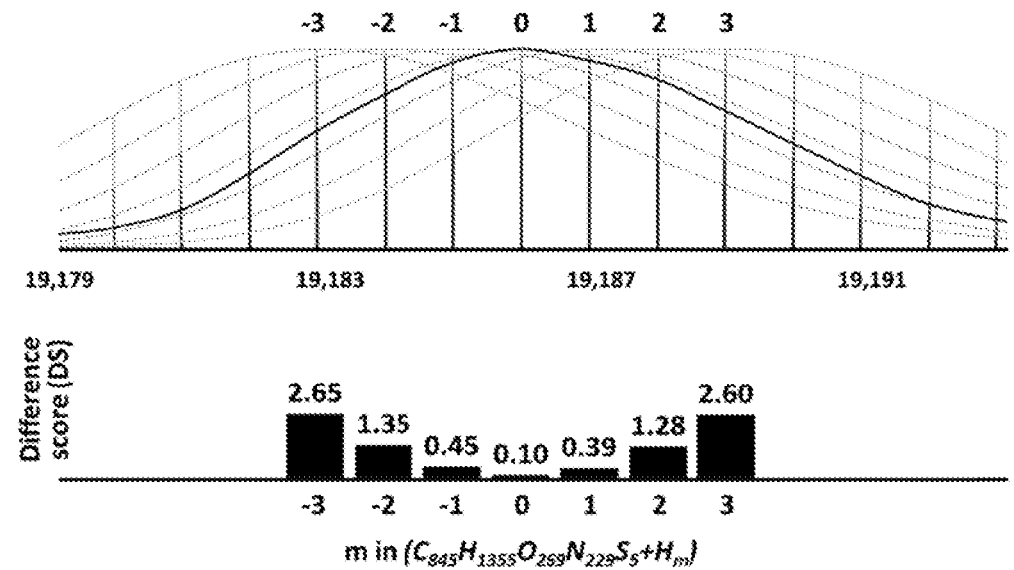
Figure 14

Humulin ($C_{257}H_{383}O_{77}N_{65}S_6$)

A chain:
  GIVEQCCTSI CSLYQLENYC N

B chain:
  FVNQHLCGSH LVEALYLVCG ERGFFYTPKT

Saizen ($C_{990}H_{1528}O_{300}N_{262}S_7$)

```
FPTIPLSRLF  DNAMLRAHRL  HQLAFDTYQE  FEEAYIPKEQ
KYSFLQNPQT  SLCFSESIPT  PSNREETQQK  SNLELLRISL
LLIQSWLEPV  QFLRSVFANS  LVYGASDSNV  YDLLKDLEEG
IQTLMGRLED  GSPRTGQIFK  QTYSKFDTNS  HNDDALLKNY
GLLYCFRKDM  DKVETFLRIV  QCRSVEGSCG  F
```

METHOD FOR VERIFYING THE PRIMARY STRUCTURE OF PROTEIN

FIELD OF THE INVENTION

The present invention is related to a method for verifying the primary structure of a protein, and in particular, to a method for verifying the primary structure of a protein using the results of high-resolution mass spectrometry.

BACKGROUND OF THE INVENTION

1. History of Protein Therapeutics

The medical use of traditional biological products such as coagulation factors, immunoglobulins or certain antibiotic is the very beginning of protein products as therapeutic agents. These biologics are mostly mixtures that are extracted from blood, plant or bacterial materials. In 1970s, recombinant DNA technology provides the possibilities of protein engineering. The concept of structure-function relationship gave rise to the first human protein therapeutic, insulin (Humulin®), invented at Genetech, developed by Eli Lilly, and approved by US Food and Drug Administration (FDA) in 1982. The idea of filling in the particular protein which is deficient in the diseased patient has led to a new trend in biopharmaceutical industry. Later on, redesigning those therapeutics with few changes to make analogs for better patient compliances, efficacy or half-life took another lead. Among protein therapeutics, antibody-based drugs are a fast growing class and the most marketed ones. The technology of chimerization and humanization of antibody has overcome the limits of treatment with rodent antibodies. Also, the easier path of harvesting human antibody using transgenic mice or phage display, as well as the industrialization of antibody manufacture, have facilitated its widespread use.

As popular as they are in pharmaceutical industry, proteins as therapeutics still have several limits. All the protein therapeutics face the same issue that oral intake is not possible because of the proteolytic digestion in human digestive system. The high production cost, which often reflects on its price, limits its access to general patient population. Recently, patent expiration of several therapeutics has started the competition between biosimilar and patent protein therapeutics. Biosimilar is referred as the particular recombinant proteins that are produced in different facilities or companies. The root "similar" implies the unrepeatable nature of protein-produced biological system between different laboratories. Finally, the delivery of protein therapeutics is limited to extracellular space like circulation system or cell surface. Thus, intracellular delivery or target therapy is now one of the most popular goals that pharmaceutical industry is interested in.

2. Quality Control (QC) of Recombinant/Therapeutic Proteins

To ensure the efficacy and safety of the active substance, characterization of biotechnological products is essential before their clinical application. Characterization of protein therapeutics includes verification of their physiochemical properties, biological activities, immunochemical properties, purities and impurities. In addition, long-term characterization of therapeutics between lots and after storage is required for evaluation of manufacturing consistency and substance stability.

In order to confirm structural characteristics, the analyses of protein primary structures are needed, including determination of amino acid sequences from recombinant DNA sequences, amino acid compositions, terminal amino acid sequences, peptide maps, the numbers and positions of sulfhydryl groups and carbohydrate contents. Physiological properties like molecular mass, isoform patterns, extinction coefficients, electrophoretic patterns, liquid chromatographic patterns and spectroscopic profiles are sometimes documented.

In addition to the active substance, impurities and contaminants need to be examined carefully. These unwanted substances can be divided into three categories: cell substrate-derived impurities, cell culture-derived impurities and downstream-derived impurities. Cell substrate-derived impurities include expression vectors, chromosomes of host cells and other nucleic acid substances. For cell culture-derived products, impurities like serum, antibiotics and media components should be taken into consideration. The downstream-derived impurities are those reagents for biochemical processing such as enzymes, chemicals, solvents and ligands.

Another group of impurities that need to be determined are product-related derivatives. These derived substances may contain a few defects compared with the original active substance, and these derivatives might be difficult to be determined even with current technologies. Such variants include truncated forms, modified forms or aggregates. Modified forms including small changes like deamidation, isomerization, mismatched disulfide linkages or altered conjugations can sometimes be identified by high performance liquid chromatography (HPLC), capillary electrophoresis or mass spectrometry. However, considering the limitations of these analytical techniques, many of these structural variations cannot be readily detected or characterized.

3. Mass Spectrometry and QC of Protein Therapeutics

Mass spectrometry (MS) has been extensively used for molecule identification by measuring mass to charge ratio (m/z) for derivation of accurate molecular mass (MM). However, for determination of a large molecule, like a recombinant protein or a therapeutic antibody, the exact mass identification becomes intricate due to the composition of high atom numbers. For years, scientists have been managing to bypass direct measurement of macromolecule with MS and developed several reductionist methodologies. This led to the development of the widely used 'bottom-up' approaches. Later on, instrumental improvements have prompted more researches to take on top down approach instead.

4. "Bottom-up" Strategy

"Bottom-up" protein analysis, in which the polypeptides are first enzymatically processed into small peptides and then analyzed with mass spectrometry analysis, has become the protein characterization strategy of choice. The benefits of its high-throughput feature and being capable of analyzing protein mixtures have made it the most commonly used among the approaches. In general, two techniques are involved in bottom-up strategy: peptide mass fingerprinting (PMF) and collision-induced dissociation (CID). With the development of new computer software systems, database searching of both PMF and CID can be easily accessed with high-throughput screening of posttranslational modifications (PTMs) or protein sequences. Bottom-up approach is favored with its high-throughput nature and has become a golden standard. However, variations in protein coverage, unpredictable artifacts and the loss of labile PTM information lead to its limited roles in profiling the full features of a biomolecule (Chen et al., *Drug Discovery Today* 16, 58-64 (2011)).

5. "Top-Down" Strategy

The concept that molecular masses of a molecule and its fragments are measured for acquisition of the needed structural information could be dated back to a century ago. There have been theories about estimation and measurement of biomolecule contents and polypeptide fragmentation with mass spectrometry. However, such analyses remained not feasible until MS techniques like electron ionization were invented. Top-down strategy, also known as intact protein analysis, is featured by direct polypeptide MS analysis without prior enzymatic digestion. The advantages of analyzing biomolecules with structural integrity are very appealing, but researchers have found it difficult to be executed due to several reasons. First, the purity of biomolecule samples and structural information are needed for the choice of the methods for proper analyses. With instrumental improvements, several options are reported to be utilized for characterizing protein primary structure with different specialties, including CID for protein sequencing, election-capture dissociation (ECD)/election-transfer dissociation (ETD) for isoaspartate measurement, ETD for disulfide bond linkage mapping and in-source decay (ISD) in a matrix-assisted laser desorption/ionization time-of flight (MALDI-TOF) MS for labile PTM analyses and potentially PEGylation site determination. For the research of conformational dynamics between therapeutics and receptor proteins, instead of classical biophysical methods, H/D exchange MS is reported for such potential. Meanwhile, ion mobility MS (IMS) is likely a new technique for higher order protein studies.

atomic masses (Table 1). The monoisotopic mass of an element is defined by the atomic mass of the stable isotope with the highest abundance in nature. For example, the monoisotopic masses of these five elements are the atomic masses of $^{12}C$, $^{1}H$, $^{14}N$, $^{16}O$ and $^{32}S$, respectively. For a particular element, since the other atomic isotopes have one or more extra neutrons in their nuclei, such atomic isotopes should be heavier than the one with the monoisotopic masses. Thus, the atomic isotope with the monoisotopic mass can be considered to be the lightest among all atomic isotope variants (see Table 1 below).

For a molecule like protein, its monoisotopic mass is the molecular mass of the isotopologue that contains exclusively atomic isotopes with monoisotopic masses for the elements, i.e. $^{12}C$, $^{1}H$, $^{14}N$, $^{16}O$ and $^{32}S$. Since this isotopologue contains the only the lightest atomic isotopes, this homologue should be the lightest among all of the possible isotopologues for a protein. Since neutrons have the mass of 1 Da, addition of one extra neutron should cause a 1 Da increment in the molecular mass of an isotopologue no matter which element has this extra neutron added. In other words, the inclusion of extra neutron leads to stepwise increments in molecular masses for these isotopologues. The different isotopologues with the same number of extra neutrons should have very similar molecular masses, and they are usually detected together at only one position as one signal or peak in the ion cluster in a high-resolution mass spectrum. Although a protein molecule can have numerous combinations of atomic isotopes, these isotopologues should cluster into groups primarily based on the number of extra neutrons. Hence, these isotopologues are detected as an ion cluster in high-resolution mass spectra, which consist of signals with 1 Da mass differences.

TABLE 1

The order of stable isotopes of common elements for a protein

| | | Stable isotopes | | | | | | | | |
|---|---|---|---|---|---|---|---|---|---|---|
| Element | | $1^{st}$ | | $2^{nd}$ | | $3^{rd}$ | | $4^{th}$ | | $5^{th}$ |
| C | Mr | $^{12}C$ | 12.000000 | $^{13}C$ | 13.0033548378 | $^{14}C$ | 14.003241989 | — | | — |
| | % | | 98.93 | | 1.07 | | Trace | | | |
| H | Mr | $^{1}H$ | 1.00782503207 | $^{2}H$ | 2.0141017778 | $^{3}H$ | 3.0160492777 | — | | — |
| | % | | 99.9885 | | 0.0115 | | Trace | | | |
| O | Mr | $^{16}O$ | 15.99491461956 | $^{17}O$ | 16.99913170 | $^{18}O$ | 17.9991610 | — | | — |
| | % | | 99.757 | | 0.038 | | 0.205 | | | |
| N | Mr | $^{14}N$ | 14.0030740048 | $^{15}N$ | 15.0001088982 | $^{16}N$ | 16.0061017 | — | | — |
| | % | | 99.636 | | 0.364 | | Trace | | | |
| S | Mr | $^{32}S$ | 31.97207100 | $^{33}S$ | 32.97145876 | $^{34}S$ | 33.96786690 | — | $^{36}S$ | 35.96708076 |
| | % | | 94.99 | | 0.75 | | 4.25 | | | 0.01 |

6. Isotopic Distribution in High-Resolution Mass Spectrum

The isotopic distribution of an ion cluster reflects the number and probabilities of occurrence of different isotopic variants of a molecule. Under conditions of unit mass resolution, naturally occurring isotopes result in a cluster of peaks in the region of the precursor ion covering the range of a few m/z units. Those ion peaks corresponding to a molecule in a mass spectrum are named as an ion cluster, isotope distribution or isotope envelope. An ion cluster is made of a series of isotopic homologues, or isotopologues. Isotopologues are molecules differing only in their composition of atomic isotopes.

Proteins are usually made of twenty amino acids, which are in turn made of atoms from five different elements, namely carbon (C), hydrogen (H), nitrogen (N), oxygen (O) and sulfur (S). Each of these five elements has multiple atomic isotopes, and these atomic isotopes have distinct

SUMMARY OF THE INVENTION

In one aspect, the present invention provides a method for verifying the primary structure of a protein through comparative analyses between ion clusters observed in mass spectra and a series of simulated ion clusters deduced from its putative chemical formula, the method comprising the steps of: preparing a protein sample for mass spectrometric analyses; collecting mass spectra of the protein sample; obtaining master ion cluster from a plurality of ion clusters in the mass spectra; producing a series of simulated ion clusters according to the chemical formula of the protein sample; finding the best fit for the master ion cluster among the series of simulated ion clusters; and verifying if the best-fit simulated ion cluster corresponds to the chemical formula of the protein sample.

According to certain embodiments of the present invention, the protein sample is prepared through the process of removal of diverse types of modifications. According to certain embodiments of the present invention, the diverse types of modifications are that the type of modification has more than five variations of combinations at one particular amino acid residue. According to certain embodiments of the present invention, the diverse type of modifications is glycosylation at asparagine residues of proteins.

According to certain embodiments of the present invention, the protein is a monoclonal antibody, a hormone, a growth factor, a fusion protein, a cytokine, a therapeutic enzyme, a blood factor, a recombinant vaccine, or an anticoagulant.

According to the present invention, collected mass spectra are determined by any analytical instruments of mass spectrometry including but not limited from the group consisting of matrix-assisted laser desorption ionization/time of flight (MALDI-TOF), surface enhanced laser desorption ionization/time of flight (SELDI-TOF), liquid chromatography-mass spectrometry (LC-MS), liquid chromatography tandem mass spectrometry (LC-MS-MS), and electrospray ionization mass spectrometry (ESI-MS).

According to certain embodiments of the present invention, the master ion cluster is generated by location and summation of the plurality of ion clusters due to different charge states using computer algorithms.

According to certain embodiments of the present invention, the series of simulated ion clusters are generated according to the series of the chemical formulas that are produced by adding or removing several hydrogen atoms from the chemical formula of the protein sample.

According to certain embodiments of the present invention, each simulated ion cluster is generated by sequential combinations of multiple single-element ion cluster simulations whose numbers of atoms are taken from the chemical formula of the simulated ion cluster.

According to certain embodiments of the present invention, the simulated ion cluster with chemical formula $C_v H_w O_x N_y S_z$ is generated by sequential combinations of five single-element ion cluster simulations for $C_v$, $H_w$, $O_x$, $N_y$ and $S_z$, respectively.

According to certain embodiments of the present invention, $C_v$ ion cluster simulation is represented by the percentages in the entire $C_v$ simulation $P_{n,v} = A_{12_C} \cdot P_{n,v-1} + A_{13_C} \cdot P_{n-1,v-1}$, $A_{12_C}$ and $A_{13_C}$ being the natural abundances of $^{12}C$ and $^{13}C$ respectively, for the n-th putative isotopic peak in relation to the 0-th peak being the putative monoisotopic mass ($^{12}C_v$) peak; $H_w$ ion cluster simulation is represented by the percentages in the entire $H_w$ simulation $P_{n,w} = A_{1_H} \cdot P_{n,w-1} + A_{2_H} \cdot P_{n-1,w-1}$, $A_{1_H}$ and $A_{2_H}$ being the natural abundances of $^1H$ and $^2H$ respectively, for the n-th putative isotopic peak in relation to the 0-th peak being the putative monoisotopic mass ($^1H_w$) peak; $O_x$ ion cluster simulation is represented by the percentages in the entire $O_x$ simulation $P_{n,x} = A_{16_O} \cdot P_{n,x-1} + A_{17_O} \cdot P_{n-1,x-1} + A_{18_O} \cdot P_{n-2,x-1}$, $A_{16_O}$, $A_{17_O}$ and $A_{18_O}$ being the natural abundances of $^{16}O$, $^{17}O$ and $^{18}O$, respectively, for the n-th putative isotopic peak in relation to the 0-th peak being the putative monoisotopic mass ($^{16}O_x$) peak; $N_y$ ion cluster simulation is represented by the percentages in the entire $N_y$ simulation $P_{n,y} = A_{14_N} \cdot P_{n,y-1} + A_{15_N} \cdot P_{n-1,y-1}$, $A_{14_N}$ and $A_{15_N}$ being the natural abundances of $^{14}N$ and $^{15}N$ respectively, for the n-th putative isotopic peak in relation to the 0-th peak being the putative monoisotopic mass ($^{14}N_y$) peak; $S_z$ ion cluster simulation is represented by the percentages in the entire $S_z$ simulation $P_{n,x} = A_{32_S} \cdot P_{n,z-1} + A_{33_S} \cdot P_{n-1,z-1} + A_{34_S} \cdot P_{n-2,z-1} + A_{36_S} \cdot P_{n-4,z-1}$, $A_{32_S}$, $A_{33_S}$, $A_{34_S}$ and $A_{36_S}$ being the natural abundances of $^{32}S$, $^{33}S$, $^{34}S$ and $^{36}S$ respectively, for the n-th putative isotopic peak in relation to the 0-th peak being the putative monoisotopic mass ($^{32}S_z$) peak.

According to certain embodiments of the present invention, the single-element ion cluster simulations of $C_v$, $H_w$, $O_x$, $N_y$ and $S_z$ are combined by a process comprising: (i) calculating the percentages $P_{M,CH}$ of the M-th peaks in the $C_v H_w$ simulation in relation to the 0-th peak being the putative monoisotopic mass ($^{12}C_v {}^1H_w$) peak, each of which equals to $\Sigma_{i=0}^{M} P_{i,v} \times P_{(M-i),w}$; (ii) calculating the percentages $P_{M,CHO}$ of the M-th peaks in the $C_v H_w O_x$ simulation in relation to the 0-th peak being the putative monoisotopic mass ($^{12}C_v {}^1H_w {}^{16}O_x$) peak, each of which equals to $\Sigma_{i=0}^{M} P_{i,CH} \times P_{(M-i),x}$; (iii) calculating the percentages $P_{M,CHON}$ of the M-th peaks in the $C_v H_w O_x N_y$ simulation in relation to the 0-th peak being the putative monoisotopic mass ($^{12}C_v {}^1H_w {}^{16}O_x {}^{14}N_y$) peak, each of which equals to $\Sigma_{i=0}^{M} P_{i,CHO} \times P_{(M-i),y}$; (iv) calculating the percentages $P_{M,CHONS}$ the M-th peaks in the $C_v H_w O_x N_y S_z$ simulation in relation to the 0-th peak being the putative monoisotopic mass ($^{12}C_v {}^1H_w {}^{16}O_x {}^{14}N_y {}^{32}S_z$) peak, each of which equals to $\Sigma_{i=0}^{M} P_{i,CHON} \times P_{(M-i),z}$; wherein i is a non-negative integer. However, a method of the present invention is not limited to such order of combination.

According to certain embodiments of the present invention, each of the single-element ion cluster simulation is directly taken from the databases consisting of the ion cluster simulations corresponding to single-element compounds containing different numbers of atoms.

According to certain embodiments of the present invention, the best fit is discovered by finding the member in the simulated ion clusters with the smallest difference scores in comparison with the master ion cluster.

According to certain embodiments of the present invention, the difference score of each simulated ion cluster is assigned with a method like one among, but not limited to, methods such as chi-square test, Pearson's chi-square test, chi-square test with Yate's correlation, Fisher's exact test, McNemar's test and Cochran's Q test.

In another aspect, the invention provides a method for verifying the primary structure of a protein, comprising: obtaining a mass spectrum of a full-length protein; identifying from the mass spectrum a plurality of ion clusters with a mass corresponding to the full-length protein but with different charge states; calculating a master ion cluster from the plurality of ion clusters; and comparing the master ion cluster with a series of simulated ion clusters generated based on the chemical formula of the full-length protein with or without a modification, to find a best fitted simulated ion cluster. If the best fitted simulated ion cluster corresponds to a full-length protein with a specific type of modification or without modification, said full-length protein with a specific type of modification or without modification represents the verified primary structure of the protein.

The method of the present invention adopts the "top-down" strategy. That is, intact or full-length protein is used in the mass spectrometric analysis. The protein sample is only pre-treated, if desired, to remove certain complicated modifications (but not fragmentized) before subjecting to mass spectrometric analysis. Preferably, the mass spectrum is obtained through a high-resolution mass spectrometry.

According to certain preferred embodiments of the present invention, the master ion cluster is calculated by a process comprising: summing up the intensities of the most abundant peak at $(m/z)_{ma}$ of each of the plurality of ion clusters, to obtain a starting summation; summing up the intensities of the next larger isotopic peak p(+1), with an m/z larger than the $(m/z)_{ma}$ according to an average isotope spacing, of each most abundant peak, to obtain a first right summation; and summing up the intensities of the next smaller isotopic peak p(−1), with an m/z smaller than the $(m/z)_{ma}$ according to the average isotope spacing, of each most abundant peak, to obtain a first left summation. In some embodiments, a plurality of right summations of a respective plurality of isotopic peaks p(+l) are obtained, a plurality of left summations of a respective plurality of isotopic peaks p(−m) are obtained, and the starting summation, the plurality of left summations and the plurality of right summations are normalized by dividing by the largest summation among all the summations, wherein l and m each is a positive integer, the isotopic peak p(+l) is the next larger isotopic peak relative to the isotopic peak p(+(l−1)) according the average isotope spacing, and the isotopic peak p(−m) is the next smaller isotopic peak relative to the isotopic peak p(−(m−1)) according the average isotope spacing. According to one embodiment of the present invention, each of the above-mentioned intensities is normalized by dividing by the charge state of the corresponding isotopic peak before being summed up.

According to the present invention, the average isotope spacing may be about 1 Dalton. Preferably, the average isotope spacing is 1.00235 Dalton.

According to present invention, each of the series of simulated ion clusters may be generated by a process comprising: given a chemical formula $C_vH_wO_xN_yS_z$ of the full-length protein with or without a modification, combining putative ion clusters of $C_v$, $H_w$, $O_x$, $N_y$ and $S_z$ to obtained the simulated ion cluster of the full-length protein with or without the modification, wherein the putative ion cluster of $C_v$ is represented by the intensities $I_{n,v} = A_{12_C} \cdot I_{n,v-1} + A_{13_C} \cdot I_{n-1,v-1}$, $A_{12_C}$ and $A_{13_C}$ being the natural abundances of $^{12}C$ and $^{13}C$ respectively, for the n-th putative isotopic peak starting from the 0-th peak being the putative monoisotopic peak; the putative ion cluster of $H_w$ is represented by the intensities $I_{n,w} = A_{1_H} \cdot I_{n,w-1} + A_{2_H} \cdot I_{n-1,w-1}$, $A_{1_H}$ and $A_{2_H}$ being the natural abundances of $^1H$ and $^2H$ respectively, for the n-th putative isotopic peak starting from the 0-th peak being the putative monoisotopic peak; the putative ion cluster of $O_x$ is represented by the intensities $I_{n,x} = A_{16_O} \cdot I_{n,x-1} + A_{17_O} \cdot I_{n-1,x-1} + A_{18_O} \cdot I_{n-2,x-1}$; $A_{16_O}$, $A_{17_O}$ and $A_{18_O}$ being the natural abundances of $^{16}O$, $^{17}O$ and $^{18}O$ respectively, for the n-th putative isotopic peak starting from the 0-th peak being the putative monoisotopic peak; the putative ion cluster of $N_y$ is represented by the intensities $I_{n,y} = A_{14_N} \cdot I_{n,y-1} + A_{15_N} \cdot I_{n-1,y-1}$, $A_{14_N}$ and $A_{15_N}$ being the natural abundances of $^{14}N$ and $^{15}N$ respectively, for the n-th putative isotopic peak starting from the 0-th peak being the putative monoisotopic peak; and the putative ion cluster of $S_z$ is represented by the intensities $I_{n,z} = A_{32_S} \cdot I_{n,z-1} + A_{33_S} \cdot I_{n-1,z-1} + A_{34_S} \cdot I_{n-2,z-1} + A_{36_S} \cdot I_{n-4,z-1}$, $A_{32_S}$, $A_{33_S}$, $A_{34_S}$ and $A_{36_S}$ being the natural abundances of $^{32}S$, $^{33}S$, $^{34}S$ and $^{36}S$ respectively, for the n-th putative isotopic peak starting from the 0-th peak being the putative monoisotopic peak.

Preferably, the putative ion clusters of $C_v$, $H_w$, $O_x$, $N_y$ and $S_z$ are combined one by one. In one preferred embodiment of the present invention, the putative ion clusters of $C_v$, $H_w$, $O_x$, $N_y$ and $S_z$ are combined according to the positions of the peaks. For example, the putative ion clusters of $C_v$, $H_w$, $O_x$, $N_y$ and $S_z$ may be combined by a process comprising: (i) calculating the intensities $I_{M,CH}$, each of which equals to $\Sigma_{i=0}^{M} I_{i,v} \times I_{(M-i),w}$; (ii) calculating the intensities $I_{M,CHO}$, each of which equals to $\Sigma_{i=0}^{M} I_{i,CH} \times I_{(M-i),x}$; (iii) calculating the intensities $I_{M,CHON}$, each of which equals to $\Sigma_{i=0}^{M} I_{i,CHO} \times I_{(M-i),y}$; (iv) calculating the intensities $I_{M,CHONS}$, each of which equals to $\Sigma_{i=0}^{M} I_{i,CHON} \times I_{(M-i),z}$; wherein i is a non-negative integer and M is the number of putative isotopic peaks other than the putative monoisotopic peak; and wherein the intensities $I_{M,CHONS}$ represents a simulated ion cluster of the full-length protein with or without the modification. However, a method of the present invention is not limited to such order of combination.

BRIEF DESCRIPTION OF THE DRAWINGS

The foregoing summary, as well as the following detailed description of the invention, will be better understood when read in conjunction with the appended drawing. In the drawings:

FIG. 2 shows the protein sequences of the tested therapeutic, PNGase F-treated erythropoietin.

FIG. 4 shows the overall charge state distribution of PNGase F-treated Eprex and Recormon in liquid chromatographic-mass spectrometric (LC-MS) analysis.

FIG. 10 illustrates the computation of isotope distribution for intensity list construction of elements, C, H and N, using dynamic programming.

FIG. 11 illustrates the computation of isotope distribution for intensity list construction of element, O, using dynamic programming.

FIG. 12 illustrates the computation of isotope distribution for intensity list construction of element, S, using dynamic programming.

FIG. 14 illustrates the primary structure verification of de-N-glycosylated Recormon using CompareMS program.

Figure 19:
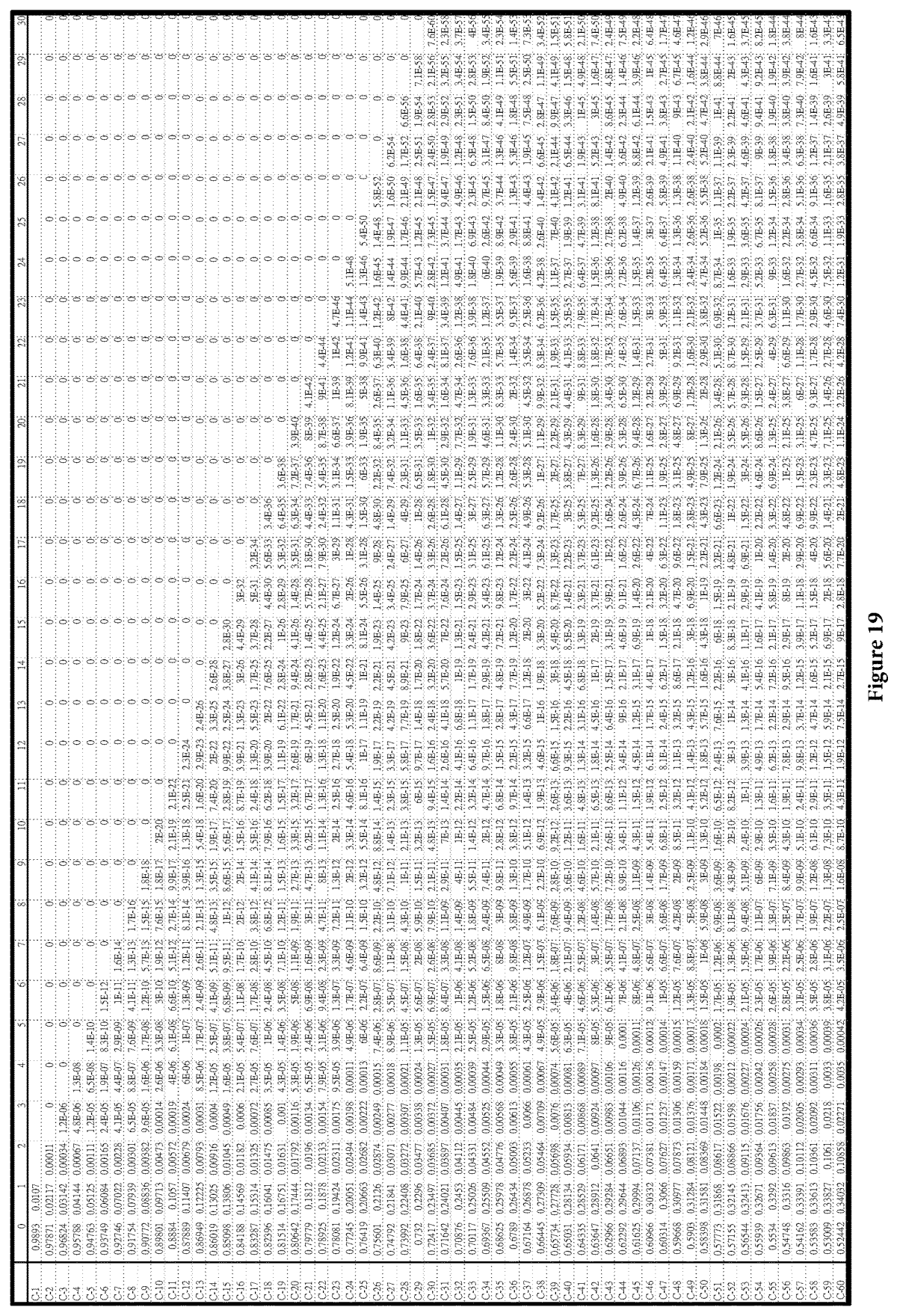

FIG. 19 shows the element-specific intensity list for carbon;

Figure 20:
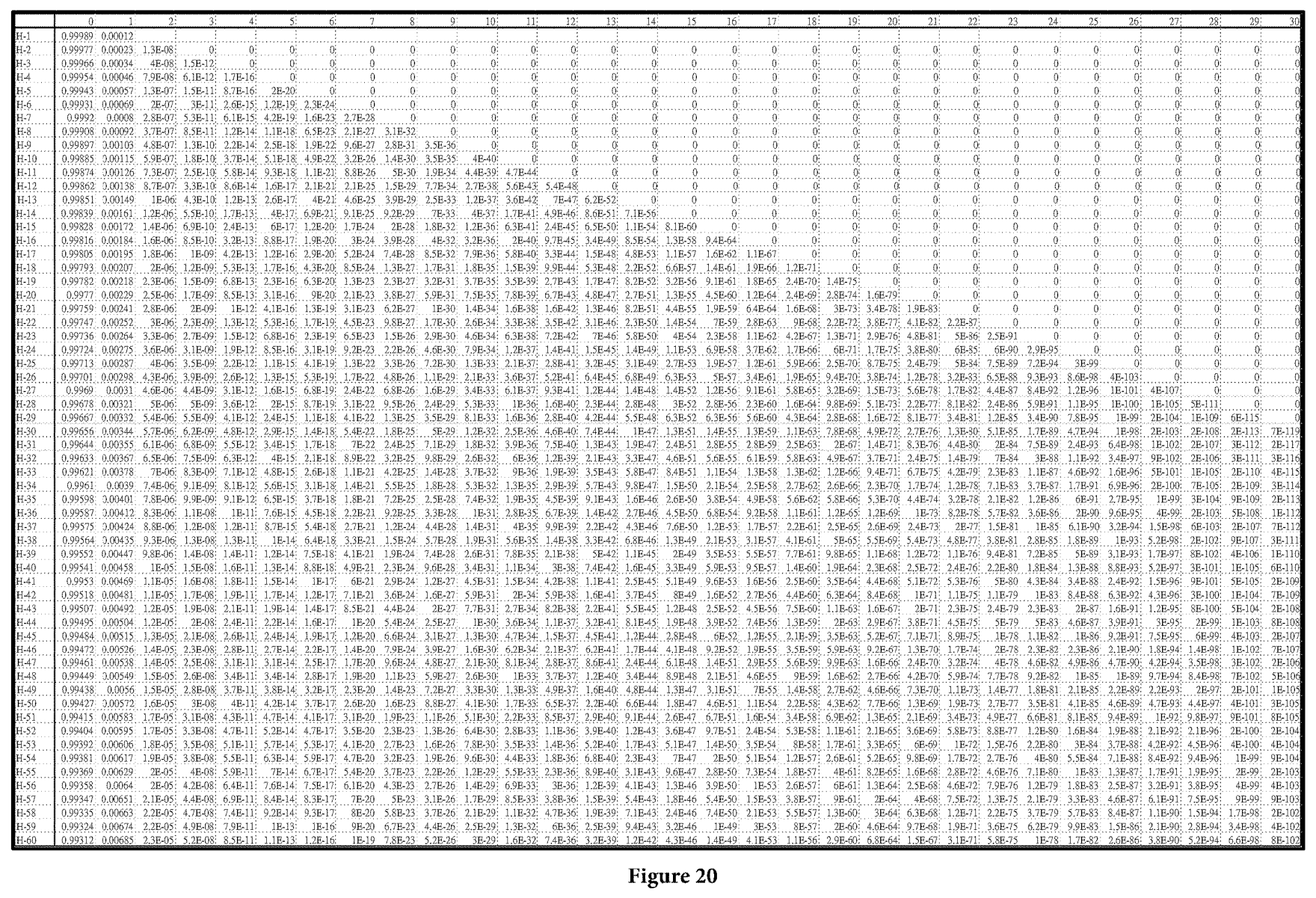

FIG. 20 shows the element-specific intensity list for hydrogen;

Figure 21:
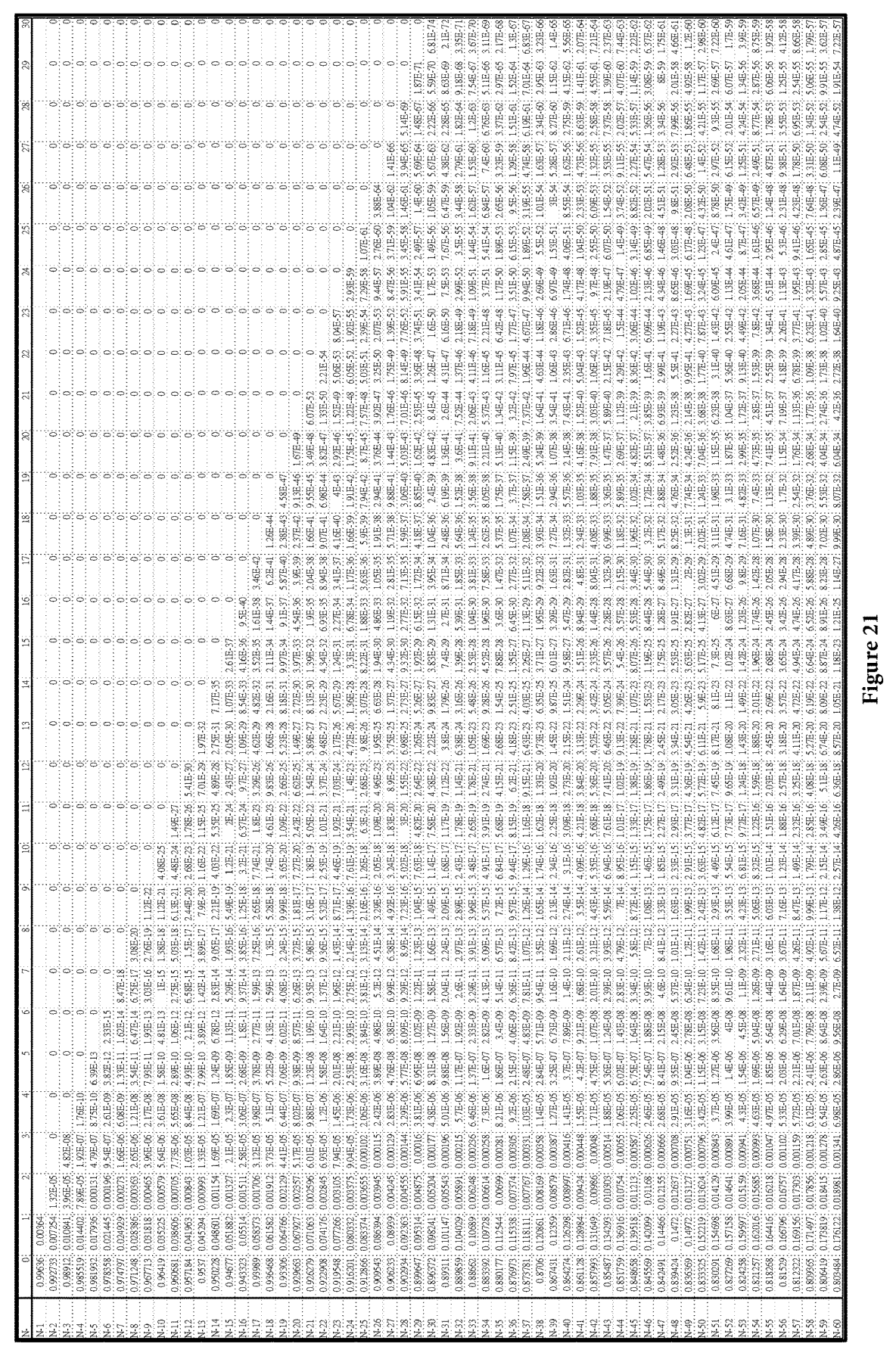

FIG. 21 shows the element-specific intensity list for nitrogen;

Figure 22:
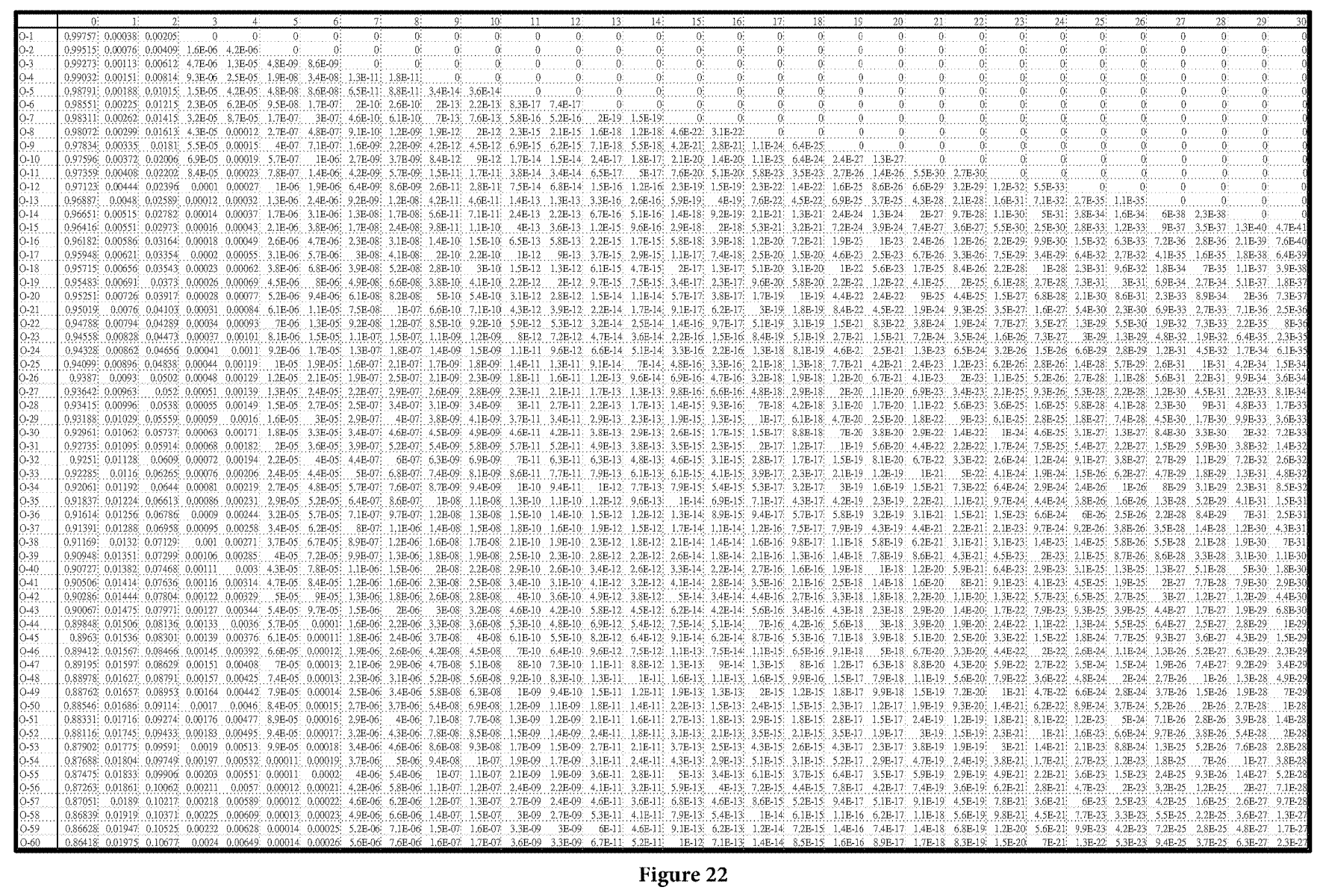

FIG. 22 shows the element-specific intensity list for oxygen; and

Figure 23:
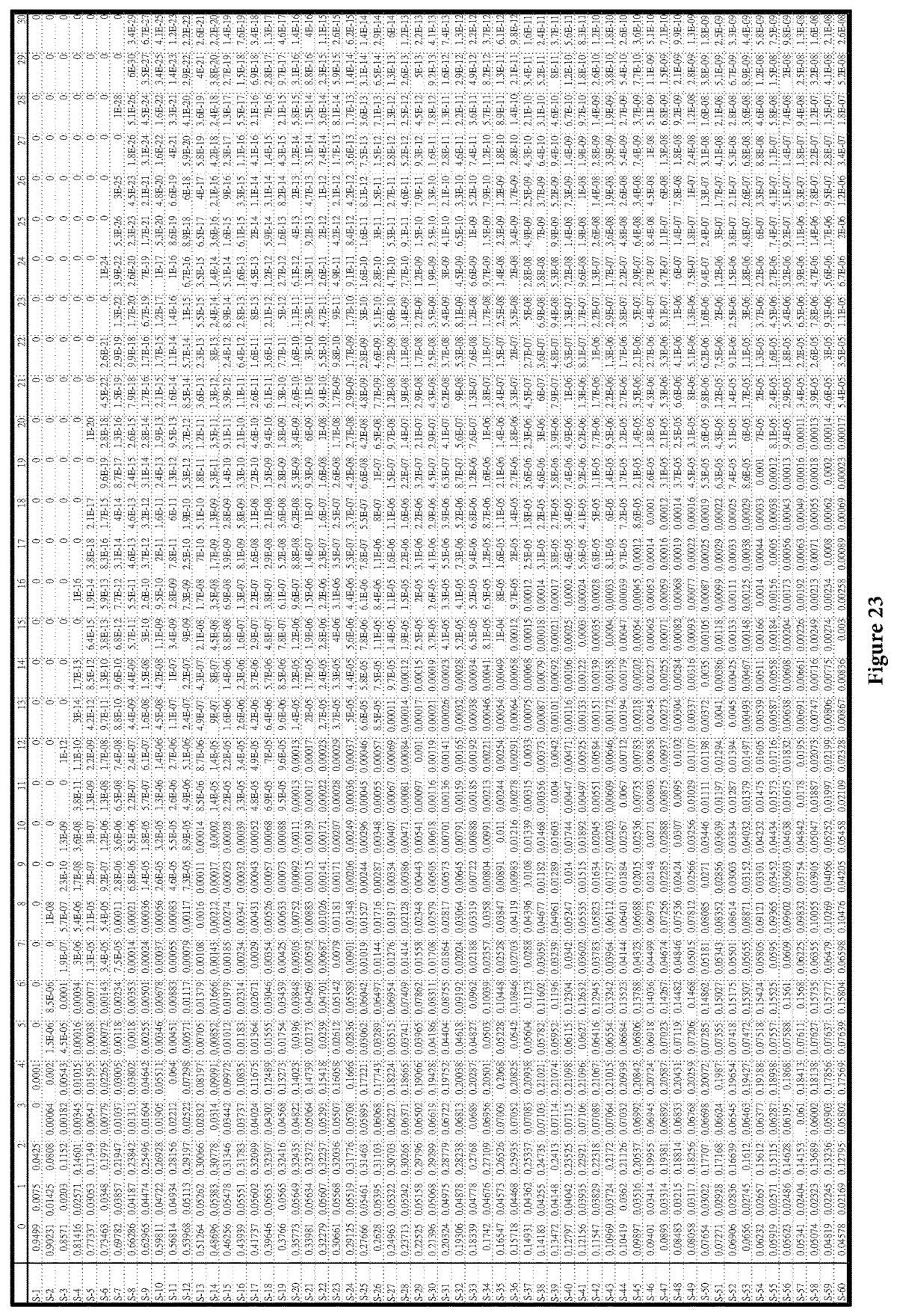

FIG. 23 shows the element-specific intensity list for sulfur.

DESCRIPTION OF THE INVENTION

Figure 1:
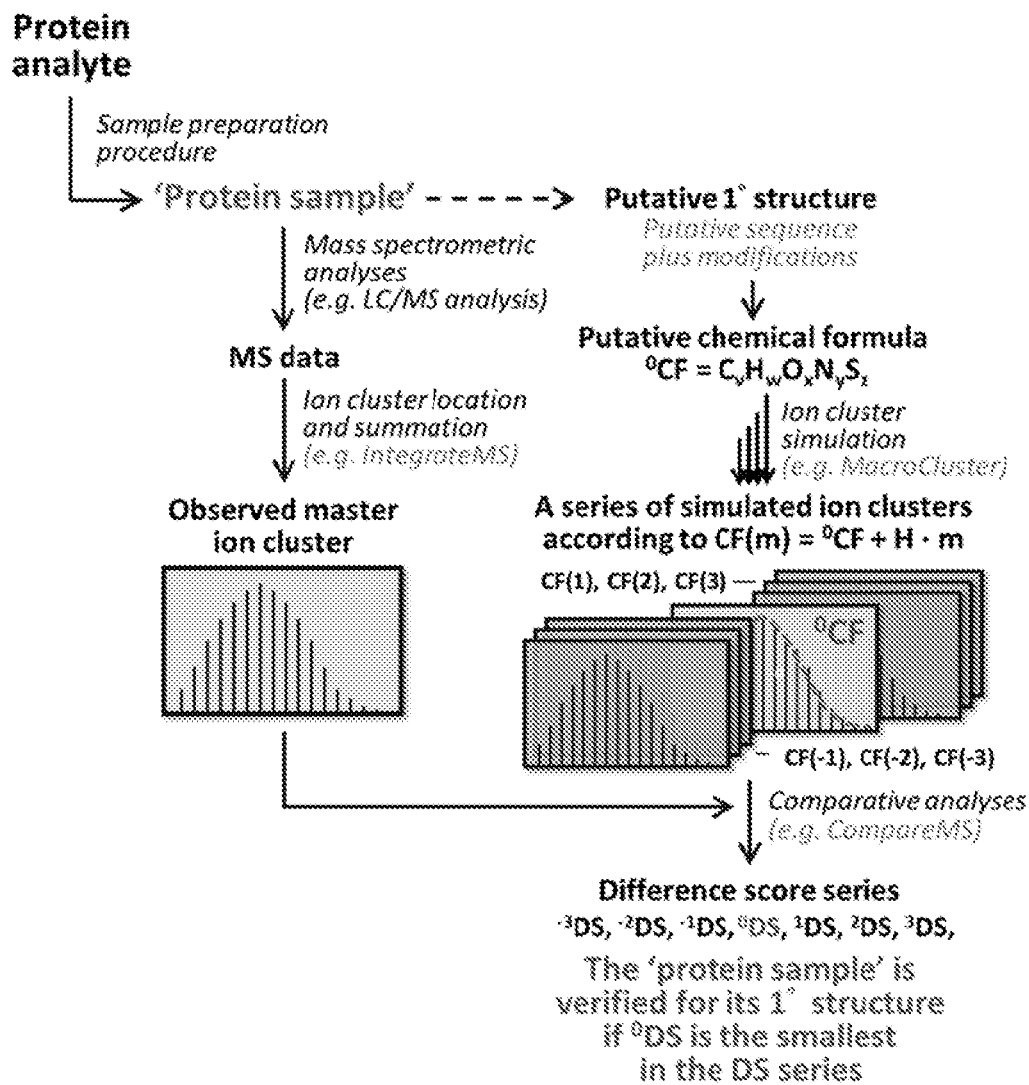
FIG. 1 provides the flowchart for verification of protein primary structure with intact protein analysis.

Unless defined otherwise, all technical and scientific terms used herein have the same meaning as commonly understood by a person skilled in the art to which this invention belongs.

In one aspect, the present invention provides a method for verifying the primary structure of a protein through comparative analyses between ion clusters observed in mass spectra and a series of simulated ion clusters deduced from its putative chemical formula, the method comprising the steps of: preparing a protein sample for mass spectrometric analyses; collecting mass spectra of the protein sample; obtaining master ion cluster from a plurality of ion clusters in the mass spectra; producing a series of simulated ion clusters according to the chemical formula of the protein; finding the best fit for the master ion cluster among the series of simulated ion clusters; and verifying if the best-fit simulated ion cluster corresponds to the chemical formula of the protein sample.

According to certain embodiments of the present invention, the protein sample is prepared through the process of removal of diverse types of modifications. According to certain embodiments of the present invention, the diverse types of modifications are that the type of modification has more than five variations of combinations at one particular amino acid residue. According to certain embodiments of the present invention, the diverse type of modifications is glycosylation at asparagine residues of proteins.

According to certain embodiments of the present invention, the protein is a monoclonal antibody, a hormone, a growth factor, a fusion protein, a cytokine, a therapeutic enzyme, a blood factor, a recombinant vaccine, or an anticoagulant.

According to the present invention, collected mass spectra are determined by any analytical instruments of mass spectrometry including but not limited from the group consisting of matrix-assisted laser desorption ionization/time of flight (MALDI-TOF), surface enhanced laser desorption ionization/time of flight (SELDI-TOF), liquid chromatography-mass spectrometry (LC-MS), liquid chromatography tandem mass spectrometry (LC-MS-MS), and electrospray ionization mass spectrometry (ESI-MS).

According to certain embodiments of the present invention, the master ion cluster is generated by location and summation of the plurality of ion clusters due to different charge states using computer algorithms.

According to certain embodiments of the present invention, the series of simulated ion clusters are generated according to the series of the chemical formulas that are produced by adding or removing several hydrogen atoms from the chemical formula of the said protein sample.

According to certain embodiments of the present invention, each simulated ion cluster is generated by sequential combinations of multiple single-element ion cluster simulations whose numbers of atoms are taken from the chemical formula of the simulated ion cluster.

According to certain embodiments of the present invention, the simulated ion cluster with chemical formula $C_vH_wO_xN_yS_z$ is generated by sequential combinations of five single-element ion cluster simulations for $C_v$, $H_w$, $O_x$, $N_y$ and $S_z$, respectively.

According to certain embodiments of the present invention, $C_v$ ion cluster simulation is represented by the percentages in the entire $C_v$ simulation $P_{n,v}=A_{12_C}\cdot P_{n,v-1}+A_{13_C}\cdot P_{n-1,v-1}$, $A_{12_C}$ and $A_{13_C}$ being the natural abundances of $^{12}C$ and $^{13}C$ respectively, for the n-th putative isotopic peak in relation to the 0-th peak being the putative monoisotopic mass ($^{12}C_v$) peak; $H_w$ ion cluster simulation is represented by the percentages in the entire $H_w$ simulation $P_{n,w}=A_{1_H}\cdot P_{n,w-1}+A_{2_H}\cdot P_{n-1,w-1}$, $A_{1_H}$ and $A_{2_H}$ being the natural abundances of $^1H$ and $^2H$ respectively, for the n-th putative isotopic peak in relation to the 0-th peak being the putative monoisotopic mass ($^1H_w$) peak; $O_x$ ion cluster simulation is represented by the percentages in the entire $O_x$ simulation $P_{n,x}=A_{16_O}\cdot P_{n,x-1}+A_{17_O}\cdot P_{n-1,x-1}+A_{18_O}\cdot P_{n-2,x-1}$, $A_{16_O}$, $A_{17_O}$ and $A_{18_O}$ being the natural abundances of $^{16}O$, $^{17}O$ and $^{18}O$, respectively, for the n-th putative isotopic peak in relation to the 0-th peak being the putative monoisotopic mass ($^{16}O_x$) peak; $N_y$ ion cluster simulation is represented by the percentages in the entire $N_y$ simulation $P_{n,y}=A_{14_N}\cdot P_{n,y-1}+A_{15_N}\cdot P_{n-1,y-1}$, $A_{14_N}$ and $A_{15_N}$ being the natural abundances of $^{14}N$ and $^{15}N$ respectively, for the n-th putative isotopic peak in relation to the 0-th peak being the putative monoisotopic mass ($^{14}N_y$) peak; $S_z$ ion cluster simulation is represented by the percentages in the entire $S_z$ simulation $P_{n,x}=A_{32_S}\cdot P_{n,z-1}+A_{33_S}\cdot P_{n-1,z-1}+A_{34_S}\cdot P_{n-2,z-1}+A_{36_S}\cdot P_{n-4,z-1}$, $A_{32_S}$, $A_{33_S}$, $A_{34_S}$ and $A_{36_S}$ being the natural abundances of $^{32}S$, $^{33}S$, $^{34}S$ and $^{36}S$ respectively, for the n-th putative isotopic peak in relation to the 0-th peak being the putative monoisotopic mass ($^{32}S_z$) peak.

According to certain embodiments of the present invention, the single-element ion cluster simulations of $C_v$, $H_w$, $O_x$, $N_y$ and $S_z$ are combined by a process comprising: (i) calculating the percentages $P_{M,CH}$ of the M-th peaks in the $C_vH_w$ simulation in relation to the 0-th peak being the putative monoisotopic mass ($^{12}C_v{}^1H_w$) peak, each of which equals to $\Sigma_{i=0}^{M}P_{i,v}\times P_{(M-i),w}$; (ii) calculating the percentages $P_{M,CHO}$ of the M-th peaks in the $C_vH_wO_x$ simulation in relation to the 0-th peak being the putative monoisotopic mass ($^{12}C_v{}^1H_w{}^{16}O_x$) peak, each of which equals to $\Sigma_{i=0}^{M}P_{i,CH}\times P_{(M-i),x}$; (iii) calculating the percentages $P_{M,CHON}$ of the M-th peaks in the $C_vH_wO_xN_y$ simulation in relation to the 0-th peak being the putative monoisotopic mass ($^{12}C_v{}^1H_w{}^{16}O_x{}^{14}N_y$) peak, each of which equals to $\Sigma_{i=0}^{M}P_{i,CHO}\times P_{(M-i),y}$; (iv) calculating the percentages $P_{M,CHONS}$ the M-th peaks in the $C_vH_wO_xN_yS_z$ simulation in relation to the 0-th peak being the putative monoisotopic mass ($^{12}C_v{}^1H_w{}^{16}O_x{}^{14}N_y{}^{32}S_z$) peak, each of which equals to $\Sigma_{i=0}^{M}P_{i,CHON}\times P_{(M-i),z}$; wherein i is a non-negative integer. However, a method of the present invention is not limited to such order of combination.

According to certain embodiments of the present invention, each of the single-element ion cluster simulation is directly taken from the databases consisting of the ion cluster simulations corresponding to single-element compounds containing different numbers of atoms.

According to certain embodiments of the present invention, the best fit is discovered by finding the member in the simulated ion clusters with the smallest difference scores in comparison with the master ion cluster.

According to certain embodiments of the present invention, the difference score of each simulated ion cluster is assigned with a method like one among, but not limited to, methods such as chi-square test, Pearson's chi-square test, chi-square test with Yate's correlation, Fisher's exact test, McNemar's test and Cochran's Q test.

In another aspect, the invention provides a method for verifying the primary structure of a protein. The method comprises the following steps: obtaining a mass spectrum of a full-length protein; identifying from the mass spectrum a plurality of ion clusters with a mass corresponding to the full-length protein but with different charge states; calculating a master ion cluster from the plurality of ion clusters; and comparing the master ion cluster with a series of simulated ion clusters generated based on the chemical formula of the full-length protein with or without a modification, to find a best fitted simulated ion cluster. If the best fitted simulated ion cluster corresponds to a full-length protein with a specific type of modification or without modification, said full-length protein with a specific type of modification or without modification represents the verified primary structure of the protein.

The term "primary structure" as used herein refers to the amino acid sequence of a protein and its (post-translational) protein modification(s).

The method of the present invention adopts the "top-down" strategy. As used herein, the term "full-length protein" refers to an intact protein or a protein which is pre-treated to remove certain complicated modifications (but not fragmentized) before subjecting to mass spectrometric analysis. For example, N-linked glycosylations can be removed by a PNGase F treatment.

Preferably, the mass spectrum is obtained through a high-resolution mass spectrometry. The high-resolution mass spectrometry includes but is not limited to a matrix-assisted laser desorption ionization/time of flight (MALDI-TOF) mass spectrometry, a surface enhanced laser desorption ionization/time of flight (SELDI-TOF) mass spectrometry, a liquid chromatography-mass spectrometry (LC-MS), a liquid chromatography tandem mass spectrometry (LC-MS-MS), or an electrospray ionization mass spectrometry (ESI-MS).

The master ion cluster is derived from the observed ion clusters in the mass spectrometry, and comprises an ordered set of normalized intensities. According to certain preferred embodiments of the present invention, certain normalized intensities are calculated by a process comprising the following steps: summing up the intensities of the most abundant peak at $(m/z)_{ma}$ of each of the plurality of ion clusters (corresponding to the full-length protein but with different charge states), to obtain a starting summation $S_S$; summing up the intensities of the next larger isotopic peak p(+1) in the plurality of ion clusters, with an m/z larger than the $(m/z)_{ma}$ according to an average isotope spacing, of each most abundant peak, to obtain a first right summation $S_{p(+1)}$; and summing up the intensities of the next smaller isotopic peak p(−1) in the plurality of ion clusters, with an m/z smaller than the $(m/z)_{ma}$ according to the average isotope spacing, of each most abundant peak, to obtain a first left summation $S_{p(-1)}$. The starting, first left and first right summations may be later normalized by the largest "intensity" (summation of intensities).

Other ordered normalized intensities may be calculated through a similar process. As such, a plurality of right summations of a respective plurality of isotopic peaks p(+l) and a plurality of left summations of a respective plurality of isotopic peaks p(−m) and may be obtained, wherein l and m each is a positive integer, the isotopic peak p(+l) is the next larger isotopic peak relative to the isotopic peak p(+(l−1)) according the average isotope spacing, and the isotopic peak p(−m) is the next smaller isotopic peak relative to the isotopic peak p(−(m−1)) according the average isotope spacing. For the normalization, the starting summation, the plurality of left summations and the plurality of right summations are divided by the largest summation $S_M$ among all the summations. l and m may be readily determined by a skilled person in the art based on actual needs. For example, detection of the left half of cluster ends as $|m|=\Delta M_N+2$, and detection of the right half ends as ions when relative abundances less than 5% is reached, wherein $\Delta M_N$ is the nominal mass difference between monoisotopic mass and most abundant mass of a protein (Chen et al., *Anal Biochem* 440, 108-113 (2013)).

Accordingly, the master ion cluster may comprise an order set of normalized intensities as follows: ($S_{p(-m)}/S_M$, $S_{p(-(m-1))}/S_M$, . . . , $S_{p(-m)}/S_M$, $S_S/S_M$, $S_{p(+1)}/S_M$, $S_{p(+(l-1))}/S_M$, $S_{p(+l)}/S_M$).

According to one preferred embodiment of the present invention, each of the observed intensities is normalized by dividing by the charge state of the corresponding isotopic peak before being summed up.

According to the present invention, the average isotope spacing may be about 1 Dalton. Preferably, the average isotope spacing is 1.00235 Dalton.

According to present invention, the master ion cluster and the series of simulated ion clusters are compared by a method selected from the group consisting of chi-square test, Pearson's chi-square test, chi-square test with Yate's correlation, Fisher's exact test, McNemar's test, and Cochran's Q test.

According to present invention, each of the series of simulated ion clusters may be generated by a process comprising: given a chemical formula $C_vH_wO_xN_yS_z$ of the full-length protein with or without a modification, combining putative ion clusters of $C_v$, $H_w$, $O_x$, $N_y$ and $S_z$ to obtained the simulated ion cluster of the full-length protein with or without the modification, wherein the putative ion cluster of $C_v$ is represented by the intensities $I_{n,v}=A_{12_C}\cdot I_{n,v-1}+A_{13_C}\cdot I_{n-1,v-1}$, $A_{12_C}$ and $A_{13_C}$ being the natural abundances of $^{12}C$ and $^{13}C$ respectively, for the n-th putative isotopic peak starting from the 0-th peak being the putative monoisotopic peak; the putative ion cluster of $H_w$ is represented by the intensities $I_{n,w}=A_{1_H}\cdot I_{n,w-1}+A_{2_H}\cdot I_{n-1,w-1}$, $A_{1_H}$ and $A_{2_H}$ being the natural abundances of $^1H$ and $^2H$ respectively, for the n-th putative isotopic peak starting from the 0-th peak being the putative monoisotopic peak; the putative ion cluster of $H_w$ is represented by the intensities $I_{n,x}=A_{16_O}\cdot I_{n,x-1}+A_{17_O}\cdot I_{n-1,x-1}+A_{18_O}\cdot I_{n-2,x-1}$, $A_{16_O}$, $A_{17_O}$ and $A_{18_O}$ being the natural abundances of $^{16}O$, $^{17}O$ and $^{18}O$ respectively, for the n-th putative isotopic peak starting from the 0-th peak being the putative monoisotopic peak; the putative ion cluster of $N_y$ is represented by the intensities $I_{n,y}=A_{14_N}\cdot I_{n,y-1}+A_{15_N}\cdot I_{n-1,y-1}$, $A_{14_N}$ and $A_{15_N}$ being the natural abundances of $^{14}N$ and $^{15}N$ respectively, for the n-th putative isotopic peak starting from the 0-th peak being the putative monoisotopic peak; and the putative ion cluster of $S_z$ is represented by the intensities $I_{n,z}=A_{23_S}\cdot I_{n,z-1}+A_{33_S}\cdot I_{n-1,z-1}+A_{34_S}\cdot I_{n-2,z-1}+A_{36_S}\cdot I_{n-4,z-1}$, $A_{32_S}$, $A_{33_S}$, $A_{34_S}$ and $A_{36_S}$ being the natural abundances of $^{32}S$, $^{33}S$, $^{34}S$ and $^{36}S$ respectively, for the n-th putative isotopic peak starting from the 0-th peak being the putative monoisotopic peak. Accordingly, each of the series of simulated ion clusters comprises an ordered set of normalized putative intensities.

Preferably, the putative ion clusters of $C_v$, $H_w$, $O_x$, $N_y$ and $S_z$ are combined one by one. In one preferred embodiment of the present invention, the putative ion clusters of $C_v$, $H_w$, $O_x$, $N_y$ and $S_z$ are combined according to the positions of the peaks. For example, the putative ion clusters of $C_v$, $H_w$, $O_x$, $N_y$ and $S_z$ may be combined by a process comprising: (i) calculating the intensities $I_{M,CH}$, each of which equals to $\Sigma_{i=0}^{M} I_{i,v} \times I_{(M-i),w}$; (ii) calculating the intensities $I_{M,CHO}$, each of which equals to $\Sigma_{i=0}^{M} I_{i,CH} \times I_{(M-i),x}$; (iii) calculating the intensities $I_{M,CHON}$, each of which equals to $\Sigma_{i=0}^{M} I_{i,CHO} \times I_{(M-i),y}$; (iv) calculating the intensities $I_{M,CHONS}$, each of which equals to $\Sigma_{i=0}^{M} I_{i,CHON} \times I_{(M-i),z}$; wherein i is a non-negative integer and M is the number of putative isotopic peaks other than the putative monoisotopic peak; and wherein the intensities $I_{M,CHONS}$ represents a simulated ion cluster of the full-length protein with or without the modification. However, a method of the present invention is not limited to such order of combination.

The present invention also includes the following Embodiments:

1. A method for verifying the primary structure of a protein comprising:

obtaining a mass spectrum of a full-length protein;

identifying from the mass spectrum a plurality of ion clusters with a mass corresponding to the full-length protein but with different charge states;

calculating a master ion cluster from the plurality of ion clusters; and comparing the master ion cluster with a series of simulated ion clusters generated based on the chemical formula of the full-length protein with or without a modification, to find a best fitted simulated ion cluster.

2. The method of Embodiment 1, wherein the master ion cluster is calculated by a process comprising: summing up the intensities of the most abundant peak at $(m/z)_{ma}$ of each of the plurality of ion clusters, to obtain a starting summation; summing up the intensities of the next larger isotopic peak p(+1), with an m/z larger than the $(m/z)_{ma}$ according to an average isotope spacing, of each most abundant peak, to obtain a first right summation; and summing up the intensities of the next smaller isotopic peak p(−1), with an m/z smaller than the $(m/z)_{ma}$ according to the average isotope spacing, of each most abundant peak, to obtain a first left summation.

3. The method of claim 2, wherein a plurality of right summations of a respective plurality of isotopic peaks p(+l) are obtained, a plurality of left summations of a respective plurality of isotopic peaks p(−m) are obtained, and the starting summation, the plurality of left summations and the plurality of right summations are normalized by dividing by the largest summation among all the summations, wherein l and m each is a positive integer, the isotopic peak p(+l) is the next larger isotopic peak relative to the isotopic peak p(+(l−1)) according the average isotope spacing, and the isotopic peak p(−m) is the next smaller isotopic peak relative to the isotopic peak p(−(m−1)) according the average isotope spacing.

4. The method of Embodiment 2 or 3, wherein each of the intensities is normalized by dividing by the charge state of the corresponding isotopic peak before being summed up.

5. The method of Embodiment 2, wherein the average isotope spacing is about 1 Dalton.

6. The method of Embodiment 5, wherein the average isotope spacing is 1.00235 Dalton.

7. The method of Embodiment 1, wherein the mass spectrum is obtained through a high-resolution mass spectrometry.

8. The method of Embodiment 1, wherein the master ion cluster and the series of simulated ion clusters are compared by a method selected from the group consisting of chi-square test, Pearson's chi-square test, chi-square test with Yate's correlation, Fisher's exact test, McNemar's test, and Cochran's Q test.

9. The method of any of Embodiments 1-8, wherein each of the series of simulated ion clusters is generated by a process comprising: given a chemical formula $C_vH_wO_xN_yS_z$ of the full-length protein with or without a modification, combining putative ion clusters of $C_v$, $H_w$, $O_x$, $N_y$ and $S_z$ to obtained the simulated ion cluster of the full-length protein with or without the modification, wherein the putative ion cluster of $C_v$ is represented by the intensities $I_{n,v}=A_{12_C} \cdot I_{n,v-1}+A_{13_C} \cdot I_{n-1,v-1}$, $A_{12_C}$ and $A_{13_C}$ being the natural abundances of $^{12}C$ and $^{13}C$ respectively, for the n-th putative isotopic peak starting from the 0-th peak being the putative monoisotopic peak; the putative ion cluster of $H_w$ is represented by the intensities $I_{n,w}=A_{1_H} \cdot I_{n,w-1}+A_{2_H} \cdot I_{n-1,w-1}$, $A_{1_H}$ and $A_{2_H}$ being the natural abundances of $^1H$ and $^2H$ respectively, for the n-th putative isotopic peak starting from the 0-th peak being the putative monoisotopic peak; the putative ion cluster of $O_x$ is represented by the intensities $I_{n,x}=A_{16_O} \cdot I_{n,x-1}+A_{17_O} \cdot I_{n-1,x-1}+A_{18_O} \cdot I_{n-2,x-1}$, $A_{16_O}$, $A_{17_O}$ and $A_{18_O}$ being the natural abundances of $^{16}O$, $^{17}O$ and $^{18}O$ respectively, for the n-th putative isotopic peak starting from the 0-th peak being the putative monoisotopic peak; the putative ion cluster of $N_y$ is represented by the intensities $I_{n,y}=A_{14_N} \cdot I_{n,y-1}+A_{15_N} \cdot I_{n-1,y-1}$, $A_{14_N}$ and $A_{15_N}$ being the natural abundances of $^{14}N$ and $^{15}N$ respectively, for the n-th putative isotopic peak starting from the 0-th peak being the putative monoisotopic peak; and the putative ion cluster of $S_z$ is represented by the intensities $I_{n,z}=A_{32_S} \cdot I_{n,z-1}+A_{33_S} \cdot I_{n-1,z-1}+A_{34_S} \cdot I_{n-2,z-1}+A_{36_S} \cdot I_{n-4,z-1}$, $A_{32_S}$, $A_{33_S}$, $A_{34_S}$ and $A_{36_S}$ being the natural abundances of $^{32}S$, $^{33}S$, $^{34}S$ and $^{36}S$ respectively, for the n-th putative isotopic peak starting from the 0-th peak being the putative monoisotopic peak.

10. The method of Embodiment 9, wherein the putative ion clusters of $C_v$, $H_w$, $O_x$, $N_y$ and $S_z$ are combined one by one.

11. The method of Embodiment 9, wherein the putative ion clusters of $C_v$, $H_w$, $O_x$, $N_y$ and $S_z$ are combined according to the positions of the peaks.

12. The method of Embodiment 10 or 11, wherein the putative ion clusters of $C_v$, $H_w$, $O_x$, $N_y$ and $S_z$ are combined by a process comprising: (i) calculating the intensities $I_{M,CH}$, each of which equals to $\Sigma_{i=0}^{M} I_{i,v} \times I_{(M-i),w}$; (ii) calculating the intensities $I_{M,CHO}$, each of which equals to $\Sigma_{i=0}^{M} I_{i,CH} \times I_{(M-i),x}$; (iii) calculating the intensities $I_{M,CHON}$, each of which equals to $\Sigma_{i=0}^{M} I_{i,CHO} \times I_{(M-i),y}$; (iv) calculating the intensities $I_{M,CHONS}$, each of which equals to $\Sigma_{i=0}^{M} I_{i,CHON} \times I_{(M-i),z}$; wherein i is a non-negative integer and M is the number of putative isotopic peaks other than the putative monoisotopic peak; and wherein the intensities $I_{M,CHONS}$ represents a simulated ion cluster of the full-length protein with or without the modification.

13. A method according to Embodiment 1, wherein the said series of simulated ion clusters correspond to the series of the chemical formulas that are produced by adding or removing several hydrogen atoms from the chemical formula of the said protein sample.

14. A method according to Embodiment 13, wherein each ion cluster member in the said series of simulated ion cluster is computationally generated by combination of multiple single-element ion clusters each of which has the number of atoms the same as that of chemical formula of the said ion cluster member.

15. A method according to Embodiment 14, wherein said ion cluster member results from the sequential pairwise combinations of single-element ion clusters based on the principle that isotopologues with the same position number in the said ion cluster member are integrated together in terms of the percentages in the ion cluster and weighted molecular masses.

16. A method according to Embodiment 15, wherein said integration of percentages of isotopologues in the ion cluster is the summation of all percentages of all isotopologues with the same position number.

17. A method according to Embodiment 15, wherein said molecular masse are the result of the equation:

$$(MM_1 \times P_1 + MM_2 \times P_2)/(P_1 + P_2)$$

where $MM_1$ and $MM_2$ are the molecular masses and $P_1$ and $P_2$ are the percentages of isotopologues in the first and second ion clusters, respectively, before integration.

18. A method according to Embodiment 15, wherein the said position number for each multi-element isotopologue is equal to the result of the following equation:

$$\Sigma_{i=2}^{5}[(\Sigma_j {}_iN_{e(j)}) \times (i-1)]$$

where ${}_iN_{e(j)}$ is the number of the ith lightest isotope of jth element, e(j), included in the said multi-element isotopologue.

19. A method according to Embodiment 18, wherein the i is the rounded integer of $(MM_I - MM_{MN})$ where $MM_I$ is the molecular mass of the said isotope I and $MM_{MN}$ is the monoisotopic mass of the said element.

20. A method according to Embodiment 18, wherein the second (2nd) lightest isotopes, as i=2, are $^{13}C$, $^{2}H$, $^{15}N$, $^{17}O$, $^{33}S$; the third (3rd) lightest isotopes, as i=3, are $^{14}C$, $^{3}H$, $^{16}N$, $^{18}O$, $^{34}S$; the fourth (4th) lightest isotope, as i=4, is $^{35}S$; and the fifth (5th) lightest isotope, as i=5, is $^{36}S$ 21. A method according to Embodiment 14, wherein the production of each single-element ion cluster is accomplished based on the principle that isotopologues with same position number in the said single-element ion cluster are integrated together in terms of the percentages in the ion cluster and weighted molecular masses.

22. A method according to Embodiment 21, wherein the position number of each single-element isotopologue is equal to the result of the following equation:

$$\Sigma_{i=2}^{5}[(\Sigma_i {}_iN) \times (i-1)]$$

where ${}_iN$ is the number of the ith lightest isotope of the said element included in the said single-element isotopologue.

23. A method according to Embodiment 22, wherein the i is the rounded integer of $(MM_I - MM_{MN})$ where $MM_I$ is the molecular mass of the said isotope I and $MM_{MN}$ is the monoisotopic mass of the said element.

24. A method according to Embodiment 14, wherein each of the said single-element ion clusters is directly taken from the databases consisting the simulated ion clusters for single-element compounds containing different numbers of atoms.

The present invention is further illustrated by the following examples, which are provided for the purpose of demonstration rather than limitation.

Example 1. The Flowchart for Verification of Protein Primary Structure

Protein sample with or without previous sample preparation is analyzed using mass spectrometry and MS data are processed with algorithms e.g. in-house IntegrateMS which implements ion cluster location and summation to produce the observed master ion cluster. Meanwhile, the putative primary(1°) structure of the protein sample, including amino acid sequence and modicidations, is converted to the expected chemical formula $C_vH_wO_xN_yS_z$ ($^{0}CF$). To verify the chemical formula of the protein sample, a series of simulated ion clusters are constructed/calculated by programs, e.g. in-house Macro Cluster according to the chemical formula $CF(m) = {}^{0}CF + H \cdot m$ where m ranges from −3 to +3. Finally, the algorithm e.g. in-house CompareMS is used to compare the master ion cluster with each of the simulated ion clusters to give different score ($^{m}DS$) series for the simulated ion clusters for CF(m). The primary structure of the protein sample is verified only if $^{0}DS$ is the smallest score in the entire DS series (See FIG. 1).

Verification of the primary structure, including amino acid sequence and posttranslational modifications (PTMs), is important for quality evaluation of a protein therapeutic. While protein modifications are key elements of protein structure, and usually are associated with particular functions, it remains a grand challenge to evaluate such sophisticated structures present in protein therapeutics. Particularly, protein modifications causing small changes in molecular masses, such as disulfides, amidations and deamidations, cannot be analyzed properly using conventional reductionist approach. On the contrary, documentation of the molecular mass of a protein therapeutic using mass spectrometry can serve as the first step to confirm its expected chemical formula. While high-resolution mass spectrometry can be applied to discern the details of protein therapeutics, we currently have no adequate knowledge as well methodologies to properly analyze their primary structures. We have implemented informatics methods to help understand how to deduce monoisotopic masses of protein therapeutics based on the characterization of most abundant masses in ion clusters (Chen et al., *Anal Biochem* 440, 108-113 (2013)). In this process, we found that informatics methods that simulate ion cluster formation would be essential for development of methods that directly verify protein primary structure, especially those protein modifications with small changes of molecular masses, such as disulfide bond formation, Gln/Asn deamidation or Glu/Asp amidation.

To test our hypothesis, we streamline the analytical procedure and establish informatics-based methods to deduce the likely primary structure of protein therapeutics by matching the master ion cluster with a series of simulated ion clusters generated based on the chemical formulas that are produced by adding or removing several hydrogen atoms from the chemical formula of the protein sample.

The protein sample, with or without pre-treatment, is first analyzed with high-resolution mass spectrometry. The mass spectrometric data are processed using programs e.g. IntegrateMS to obtain a master ion cluster through computationally merging ion clusters identified from the protein sample but with different charge states. The putative chemical formula $C_vH_wO_xN_yS_z$ ($^{0}CF$) of the tested protein sample is deduced based on its protein sequence and known protein modifications using softwares e.g. Macro Cluster; the same program also produces a series of simulated ion clusters based on the chemical formulas CF(m) that are produced by adding or removing several hydrogen atoms from the chemical formula of the putative primary structure $^{0}CF$. Finally, programs e.g. CompareMS are used to give a difference score ($^{m}DS$) to each of the simulated ion clusters based on its difference to the master ion cluster. The primary structure of the protein sample is validated only when the $^{0}DS$ has the smaller value in the DS series (see FIG. 1).

Example 2. Protein Sequences of the Tested Therapeutic, PNGase F-Treated Erythropoietin Primary structure information of erythropoietin with PNGase F treatment is provided to build up the baseline for establishment of simulated ion clusters. N→D indicates that three asparagine residues (N) are replaced as three aspartic acid ones (D with the underline) after enzymatic removal of N-linked glycans. The solid line shows the disulfide linkage between two cysteine residues. Trisaccharide NeuAc-Hex-HexNAc (FIG. 2A) and tetrasaccharide NeuAc-Hex-Hex- NAc-NeuAc (FIG. 2B) are two possible types of O-linked glycans on serine 126. The putative chemical formulas of de-N-glycosylated erythropoietin with a trisaccharide or a tetrasaccharide are deduced as $C_{834}H_{1338}O_{261}N_{228}S_5$ or $C_{845}H_{1355}O_{269}N_{229}S_5$, respectively.

In our studies, erythropoietin with N-oligosaccharide removed is used as an example for verification of its primary structure with our intact protein analyses. The putative therapeutic, de-N-glycosylated erythropoietin, is reported to contain 165 amino acids with three asparagines replaced as three aspartic acids (N→D) after enzymatic removal of N-linked glycans (FIGS. 2A and 2B). In addition, its protein modifications include two disulfide linkages and one O-linked glycosylation on serine 126 where it can be modified as two possible types of O-linked glycans, either trisaccharide NeuAc-Hex-HexNAc (FIG. 2A) or tetrasaccharide NeuAc-Hex-HexNAc-NeuAc (FIG. 2B). Hence, the putative chemical formulas of de-N-glycosylated erythropoietin with a trisaccharide or a tetrasaccharide are deduced as $C_{834}H_{1338}O_{261}N_{228}S_5$ or $C_{845}H_{1355}O_{269}N_{229}S_5$, respectively. Based on this information of chemical formulas, we will demonstrate our proposed method can help precisely verify the primary structure.

Figure 3:
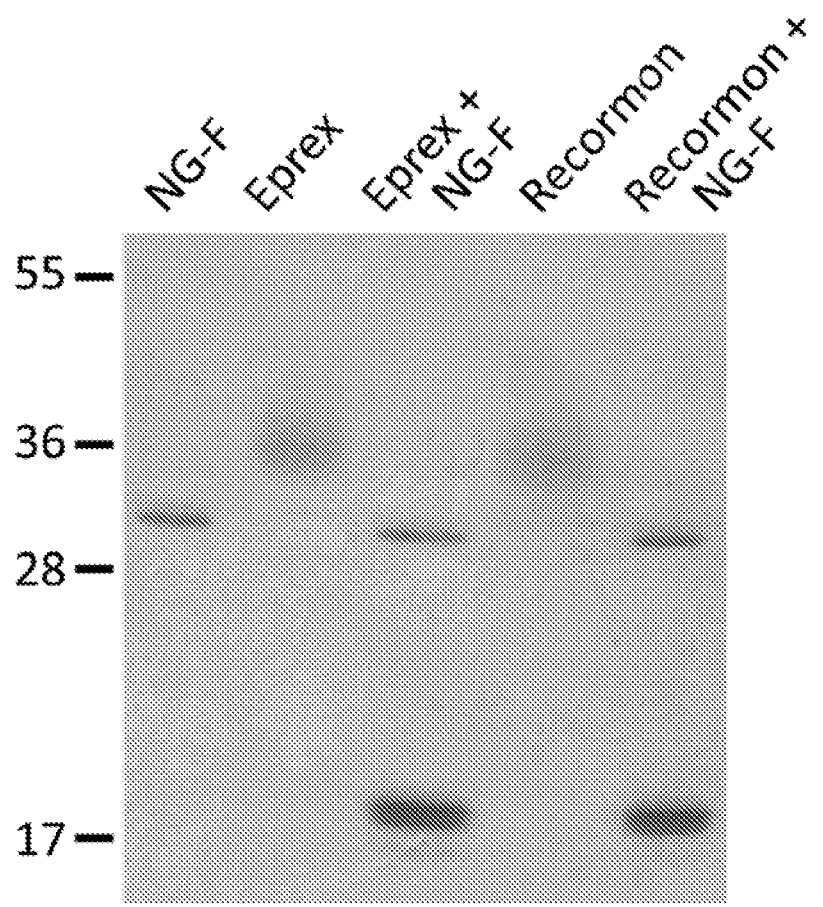
FIG. 3 shows the results of SDS-PAGE analysis of erythropoietin products with or without PNGase F treatment.

Example 3. SDS-PAGE Analysis of Erythropoietin Products with or without PNGase F Treatment Erythropoietin sample with (FIG. 3, lanes 3 and 5) or without PNGase F (NG-F) treatment (FIG. 3, lanes 2 and 4) were electrophoresed under non-reducing condition and visualized on gel by sliver staining. The numbers on the left, expressed in kilodaltons (kDa), are the positions of molecular mass markers. Lot numbers of Eprex and Recormon are EFS5600 and H0743H01, respectively.

To verify primary structure of protein therapeutics with our proposed analytical methods, human derived erythropoietin is first chosen as the tested protein. Various biologic and biosimilar erythropoietin drugs produced by recombinant DNA technology in cell culture are currently available in the market. It is still a great challenge for quality control of these protein therapeutics derived from a complex biological system. Erythropoietin is a glycoprotein with a molecular mass of about 30.4 kDa, wherein half of its molecular mass is sugar groups. The polypeptide backbone is estimated to be approximately 18 kDa. There has been reported that three sites of N-linked glycosylations on erythropoietin results in dozen of protein structures that leads to the difficulty of detection of post-translational modifications of erythropoietin product.

In order to verify whether removal of N-linked glycosylations simplifies the diversity of erythropoietin structures and helps detect other modifications easier, we performed SDS-PAGE experiment to analyze erythropoietin with or without PNGase F treatment.

Two brands of erythropoietin samples were respectively incubated with or without 3U of PNGase F (NG-F) in 25 mM ammonium bicarbonate buffer at 37° C. for 2 hours and followed by addition of 5 µl 4× sample buffer, which consists of Tris pH 6.8, 10% (w/v) SDS, 0.4% (w/v) bromophenol blue and 50% (v/v) glycerol and then heated for 10 minutes at 95° C. Those processed samples were then applied to 15% SDS-PAGE electrophoresed at 150V under non-reducing condition until tracing dye reached the bottom of the gel. The gel after electrophoresis was then developed with sliver staining.

SDS-PAGE analysis showed that erythropoietin sample before PNGase F treatment migrated as a blurred bands ranging from 30 kDa to 40 kDa under non-reducing conditions. When erythropoietin with PNGase F treatment was subjected to non-reducing SDS-PAGE analysis, it migrated like two 20 kDa polypeptides. However, their gel mobilities are closer to the known length of polypeptide of erythropoietin. These data together suggest that wide-spreading species from 30 kDa to 40 kDa are mainly caused by the variety of N-linked glycosylations. Also, these data support that PNGase F can serve as the enzyme for complete removal of complicated N-linked glycosylations.

Example 4. Overall Charge State Distribution of PNGase F-Treated Eprex and Recormon in Liquid Chromatographic-Mass Spectrometric (LC-MS) Analysis The average mass spectra of de-N-glycosylated Eprex (FIG. 4A) and Recormon (FIG. 4B) are generated within selected range of LC retention time and enlarged over the indicated mass range. The positive numbers at the top of MS signals indicate the charge states of ion clusters. The arrows mark two major signals of +15 ion clusters corresponding to de-N-glycosylated erythropoietins with a trisaccharide (I) and a tetrasaccharide (II) respectively, which is subsequently verified with our methods.

In order to characterize whether two 20 kDa polypeptides on the gel indeed resulted from O-linked glycosylations of erythropoietin after removal of N-linked glycans and to verify whether they contain two disulfide bonds, we employed liquid chromatography-mass spectrometry (LC-MS) to examine the structural details of these two polypeptides.

To examine MS profiles of these two intact polypeptides, we further subjected PNGase F-treated erythropoietin to LC-MS analyses.

The PNGase F-treated samples were analyzed in LTQ-Orbitrap hybrid tandem mass spectrometer (ThermoFisher, USA) in-lined with Agilent 1200 nanaoflow HPLC system. The HPLC system was equipped with Agilent mRP-C18 High-Recovery Protein Column (length: 100 mm; internal diameter: 0.5 mm; bead size: 5 µm) as the separating column. The mobile phase consisted of (A) 0.1% formic acid in water and (B) 0.1% formic acid in acetonitrile. The full and SIM mass spectra were collected over the mass range of m/z 200-2000 at a resolving power of 100,000. The collected data were analyzed using Xcalibur software (ThermoFisher, USA).

LC-MS analyses showed that two major protein species (I and II) were both detected for different branded erythropoietins, such as Eprex (FIG. 4A) and Recormon (FIG. 4B). The majority of these two ions had electric charges of +11 to +16. However, reverse ratios of these two major signals were observed for Eprex and Recormon. Besides, they also resulted in different patterns of charge state distributions. Based on mass determination with the previously reported $M_{ma}$-turned-$M_{mi}$ approach, major form I can primarily be confirmed as de-N-glycosylated erythropoietin with an O-linked trisaccharide, while major form II as the same one but with a tetrasaccharide. However, the mass shift of disulfide bonds is too small to elucidate its presence on these structures with the $M_{ma}$-turned-$M_{mi}$ method. Hence, the new analytical method here is developed to solve this difficulty of mass determination. All these ion signals with different charge states but from the same erythropoietin species will be identified and subsequently merged into an observed master ion cluster by using our in-house programs, IntegrateMS. The derived two observed master ion clusters will be verified with our informatics method to answer whether they are indeed as reported O-linked oligosaccharide-containing erythropoietins with two disulfide bonds.

Example 5. Workflow of IntegrateMS: To Mine for Ion Clusters and to Obtain Normalized MS of Target Protein For screening out ion clusters of target protein among different charge state $P_2$. Most abundant mass-over-charge $(m/z)_{ma}$ as $P_1$ at charge state $P_2$ is inputted as start of ion cluster fishing. Each charge state, from $P_2+N$ to $P_2-N$, has its own $(m/z)_{ma}$. If $P_1$ within $P_2$ presents in the spectrum, FullCluster Algorithm is activated to obtain full cluster at $P_2$ charge state. If not, next $P_2+N$ or $P_2-N$ is applied. For ion cluster mining at certain charge state, FullCluster Algorithm is designed to hook for $(m/z)_{ma}$ and then search for neighbor peaks with m/z of $(m/z)_{ma}+(1.00235/x) \cdot L$. If multiple peaks are detected with mass error less than 15 ppm, the maximal of $I_{L,x}$ is selected as the ion signal with position L. Detection of the left half of cluster ends as $|L|=\Delta M_N+2$, and detection of the right half ends as ions when relative abundances less than 5% is reached, wherein $\Delta M_N$ is the nominal mass difference between monoisotopic mass and most abundant mass of a protein (Chen et al., *Anal Biochem* 440, 108-113 (2013)). With FullCluster Algorithm searching out for individual clusters at different charge states, multiple ion clusters are obtained. Detected ion clusters are combined and normalized to access observed master ion cluster. x: charge state.

Figure 6:
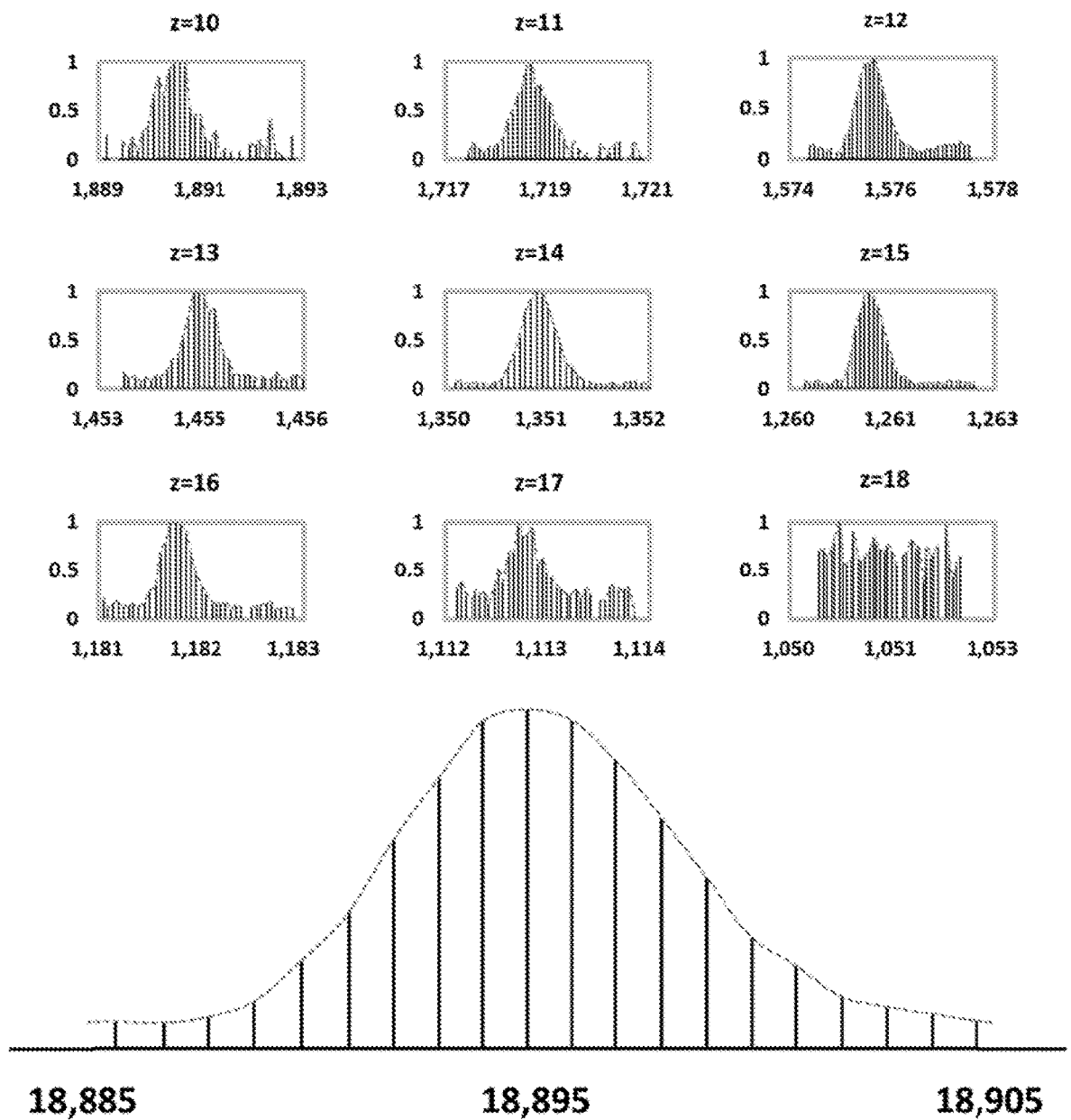
FIG. 6 shows the ion clusters of de-N-glycosylated Eprex with an O-linked trisaccharide mined out from MS raw data by IntegrateMS and the subsequent integrated master ion cluster.

Example 6. Ion Clusters of De-N-Glycosylated Eprex with an O-Linked Trisaccharide Mined Out from MS Raw Data by IntegrateMS and the Subsequent Integrated Master Ion Cluster After LC-MS analysis of supposed analyte, PNGase F-treated Eprex, mass spectrometric raw data were processed by IntegrateMS to obtain ion clusters of de-N-glycosylated Eprex with an O-linked trisaccharide at charge states from 10 to 18 (FIG. 6, dash-lined profiles above). While all the individual clusters are gathered, with summation of the signals with the same position among different charge states, observed master ion cluster derived (FIG. 6, dash-lined profile below).

Figure 7:
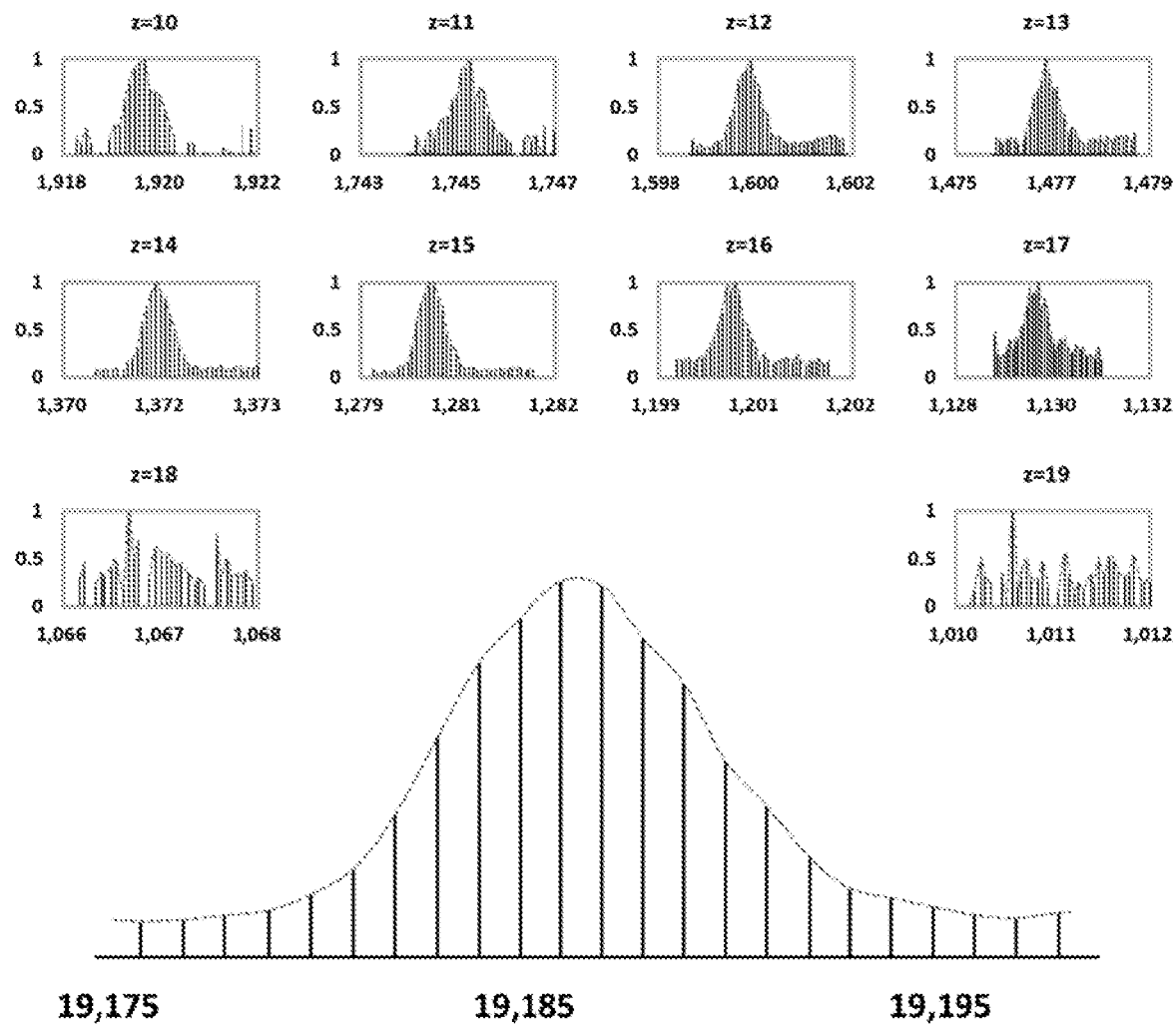
FIG. 7 shows the ion clusters of de-N-glycosylated Eprex with an O-linked tetrasaccharide mined out from MS raw data by IntegrateMS and the subsequent integrated master ion cluster.

Example 7. Ion Clusters of De-N-Glycosylated Eprex with an O-Linked Tetrasaccharide Mined Out from MS Raw Data by IntegrateMS and the Subsequent Integrated Master Ion Cluster After LC-MS analysis of supposed analyte, PNGase F-treated Eprex, mass spectrometric raw data were processed by IntegrateMS to obtain ion clusters of de-N-glycosylated Eprex with an O-linked tetrasaccharide at charge states from 10 to 19 (FIG. 7, dash-lined profiles above). While all the individual clusters are gathered, with summation of the signals with the same position among different charge states, observed master ion cluster derived (FIG. 7, dash-lined profile below).

Example 8. Program IntegrateMS

When protein molecules are ionized through electrospray ionization, these molecules can take different numbers of protons to become molecular ions with various positive charge states. As molecular ions with a particular charge state move closely together in the mass analyzer, they should become one ion cluster in the high-resolution mass spectrum. When different numbers of protons are taken, there should be multiple ion clusters observed in the mass spectrum even for a protein with one single chemical formula (Zhang et al., *J Am Soc Mass Spectrom* 9, 225-33 (1998)). In our previous version, we have chosen the ion cluster with the highest signal for later CompareMS analyses (data not shown). We have observed that most of these ion clusters did not have a smooth profile and many were even defective, lacking a few peaks in the cluster. Intriguingly, when these clusters are put together to become one integrated one, this synthetic cluster has a much smoother profile. Thus, this significant improvement upon signal integration prompted us to develop a computer program that can automatically detect those clusters that are from the same protein molecules but have different charge states.

Figure 5:
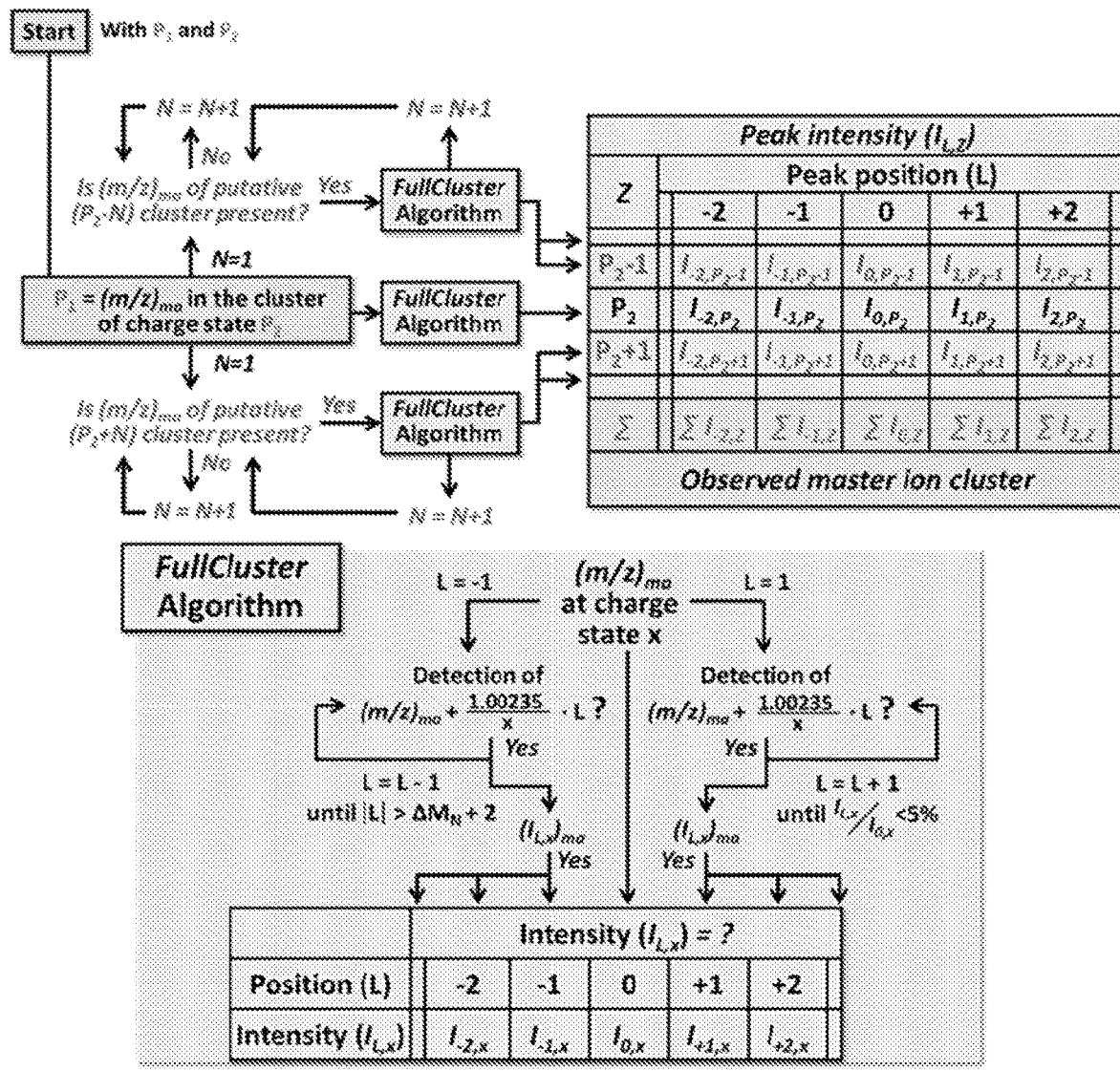
FIG. 5 shows the workflow of IntegrateMS: to mine for ion clusters and to obtain normalized MS of target protein.

Automatic mining out ion clusters of target MS signals from different charge states is developed (FIG. 5). There are two parameters $P_1$ and $P_2$ that are considered for IntegrateMS program when LC-MS data of a protein sample are analyzed. $P_1$ is the m/z value of the highest signal among the cluster, or $(m/z)_{ma}$, and $P_2$ is the charge state of this m/z value. First, $P_1$ and $P_2$ are used to check whether the clusters at different charge states are present, on the basis of the detection of $(m/z)_{ma}$ for each ion cluster. When the signal of $(m/z)_{ma}$ is present, FullCluster algorithm is started.

FullCluster algorithm assumes the mass difference between neighboring signals in a cluster is 1.00235, which is derived using Averagine concept (Chen et al., *Anal Biochem* 440, 108-113 (2013); Senko et al., *J Am Soc Mass Spectrom* 6, 229-233 (1995)). For the cluster with the charge state of $P_2$, we will use the mass step $(1.00235/P_2) \times L$ to examine whether other peaks in the cluster are present. For the left half of the cluster, L is a negative integer that ranges from $-1$ to $(\Delta M_N+2)$. This $\Delta M_N$ value is the nominal mass difference between monoisotopic mass and most abundant mass of a protein (Chen et al., *Anal Biochem* 440, 108-113 (2013)). $\Delta M_N$ per se is a function of protein molecular mass, specifically $\Delta M_N=0.63 \times M_{ma}$ (KDa)$-0.62$, according to our calculation (Chen et al., *Anal Biochem* 440, 108-113 (2013)). For the right half of the cluster, L is a positive integer, ranging from $+1$ to the number whose signal intensity is smaller than 0.05 of the intensity of $(m/z)_{ma}$, i.e. $I_{o,P2}$. When these signals are found present, each of their signal intensities, $I_{L,P2}$, will be recorded. Those clusters with their $(m/z)_{ma}$ detected are subjected to FullCluster analyses as well. Thus, all of the clusters are aligned according to their L values, and the signal intensities with the same L value are added together, which produces the master observed ion cluster (FIG. 5).

Sample Results Using Program IntegrateMS

We applied IntegrateMS to analyze the data acquired for de-N-glycosylated erythropoietins. Erythropoietin is a 18-KDa construct and its primary structure, including one O-linked glycosylation and two disulfide bonds, has been primarily verified using our $M_{ma}$-turned-$M_{mi}$ method (Data not shown) (Chen et al., *Anal Biochem* 440, 108-113 (2013)). As mentioned, there were some problems in locating the correct $M_{ma}$, and thus we would like to confirm these results on IntegrateMS analyses to generate master ion clusters. The results through integration were later analyzed with subsequent programs.

For integration of de-N-glycosylated Eprex with an O-linked trisaccharide, we used $(m/z)_{ma}=1350.629$ as the $P_i$ parameter and charge state z=14 as the parameter $P_2$. IntegrateMS program found nine $(m/z)_{ma}$ values from charge states 10 to 18. With these $(m/z)_{ma}$ values, nine ion clusters were profiled (FIG. 6). Among these ion clusters, those at states +14 to +16 have rather smooth profiles. However, the profiles of others were not as perfect and, particularly, the +10, +17 and +18 clusters have many defects. Upon integration, the master ion cluster finally has the best distribution pattern. Also for integration of de-N-glycosylated Eprex with an O-linked tetrasaccharide, we used 1280.126 and 15 as the $P_1$ and $P_2$ for identification of all related ion clusters. As ten $(m/z)_{ma}$ values were found by the program, they were all mined out as non-smooth clusters (FIG. 7). While the master ion cluster kept a crescendo- and decrescendo-pattern intact, the overall pattern was not as smooth.

Altogether, while these deductions show the effectiveness of IntegrateMS in completion of cluster profiling, the much smoother profiles of master ion clusters highlight the necessity of collective consideration of all molecular ions even at diverse charge states.

Example 9. Simulated Isotope Distribution can be Computed by Intensity List-Based Cluster Deduction by MacroCluster Prior to ion cluster prediction, the intensity of isotope distributions for numerous numbers of each elements, C, H, O, N and S, were separately computed and recorded in element-specific intensity lists (FIGS. 19-23). For simulated ion cluster analyses, to establish simulated clusters of a protein, the imported primary structure information such as sequence and PTM are summed up as chemical formula $C_vH_wO_xN_yS_z$. The isotope distribution of $C_v$, $H_w$, $O_x$, $N_y$ and $S_z$ are obtained by looking up element-specific intensity lists. The selected single-element ion clusters by look-up table procedure are processed with following Merger algorithm to gain the simulated ion cluster of the putative protein.

Example 10. Computation of Simulated Ion Cluster Based on Gradually Combining Single-Element Ion Clusters by Merger Algorithm To calculate ion distribution of therapeutic with chemical formula, $C_vH_wO_xN_yS_z$, look-up table procedure is designed to obtain element-specific ion cluster based on total amount of each element within the molecule. Further, combination of each element start from merging $C_v$ and $H_w$ for $C_vH_w$ with $I_{m,CH}=\Sigma_{i=0}^{m}I_{i,C} \times I_{(m-i),H}$. The concept of merging element $O_x$, $N_y$ and $S_z$ into intermediate $C_vH_w$, $C_vH_wO_x$ and $C_vH_wO_xN_y$ are same as above with formula $I_{m,CHO}=\Sigma_{i=0}^{m}I_{i,CH} \times I_{(m-i),O}$, $I_{m,CHON}=\Sigma_{i=0}^{m}I_{i,CHO} \times I_{(m-i),N}$ and $I_{m,CHONS}=\Sigma_{i=0}^{m}I_{i,CHON} \times I_{(m-i),S}$, respectively.

Example 11. Computation of Isotope Distribution for Intensity List Construction of Elements, C, H and N, Using Dynamic Programming Among amino acid-composed elements, C, H and N have two natural isotopes. We assume the monoisotopic ion is given by peak number 0. For N, the deduction of intensity for peak number 0 can be written as $I_{0,y}=A_{14_N} \times I_{0,y-1}$, while intensity of peak number, n, can be defined as $I_{n,y}=A_{14_N} \times I_{n,y-1}+A_{15_N} \times I_{n-1,y-1}$. $A_{14_N}$, $A_{15_N}$: Natural abundances of $^{14}N$ and $^{15}N$ respectively; $I_{0,y}$: Intensity of peak number, 0, with total atom number, y. See FIG. 10.

Example 12. Computation of Isotope Distribution for Intensity List Construction of Element, O, Using Dynamic Programming The amino acid-composed element, O, has three natural isotopes, $^{16}O$, $^{17}O$ and $^{18}O$. The deduction of intensity for monoisotopic ion can be written as $I_{0,x}=A_{16_O} \times I_{0,x-1}$, while intensity of peak number, n, can be defined as $I_{n,x}=A_{16_O} \times I_{n,x-1}+A_{17_O} \times I_{n-1,x-1}+A_{18_O} \times I_{n-2,x-1}$. $A_{16_O}$, $A_{17_O}$, and $A_{18_O}$: Natural abundances of $^{16}O$, $^{17}O$ and $^{18}O$ respectively; $I_{0,x}$: Intensity of peak number, 0, with total atom number, x. See FIG. 11.

Example 13. Computation of Isotope Distribution for Intensity List Construction of Element, S, Using Dynamic Programming The amino acid-composed element, S, have four natural isotopes, $^{32}S$, $^{33}S$, $^{34}S$ and $^{36}S$. The deduction of intensity for monoisotopic ion can be written as $I_{0,z}=A_{32_S} \times I_{0,z-1}$, while intensity of peak number, n, can be defined as $I_{n,z}=A_{32_S} \times I_{n,z-1}+A_{33_S} \times I_{n-1,z-1}+A_{34_S} \times I_{n-2,z-1}+A_{36_S} \times I_{n-4,z-1}$. See FIG. 12.

Example 14. Program Macro Cluster Developed Based on a Sequential Merging Approach We have previously developed a method to deduce the monoisotopic mass of a protein therapeutic through documentation of the relationship between the monoisotopic mass ($M_{mi}$) and most abundance mass ($M_{ma}$) determined using high-resolution mass spectrometry. We found that it was sometimes difficult to perform accurate $M_{mi}$ deduction when there are several signals with similar intensities in the ion cluster. The similarity in peak intensities creates ambiguity in assignment of the $M_{ma}$ peak, and a misassigned $M_{ma}$ may lead to a major error in $M_{mi}$ determination. Thus, we are prompted to take into consideration all the signals in the ion cluster, rather than one single $M_{ma}$ signal in characterization of its protein primary structure. Hence, automatic generation of a full simulated ion cluster from input primary structure should be established.

In order to profile the simulated ion cluster, we first needed to develop methods that can calculate the relative abundances of different isotopologues that are made of isotopes of five elements, including carbon (C), hydrogen (H), nitrogen (N), oxygen (O) and sulfur (S). Then, these methods need to sum together the abundances of those isotopologues with molecular masses too close to be resolved by mass spectrometry. This summation process is facilitated by the fact that the mass differences between the smaller isotope (the $M_{mi}$ isotope) and other isotopes (non-$M_{mi}$ isotopes) for any element is very close to 1 Dalton or its multiples. Specifically, $^{13}C$-$^{12}C$ mass difference is 1.003355 Da; $^{2}H$-$^{1}H$ difference is 1.006277 Da; $^{17}O$-$^{16}O$ and $^{18}O$-$^{16}O$ differences are 1.004218 and 2.004246 Da, respectively; $^{15}N$-$^{14}N$ difference is 0.997035 Da; $^{33}S$, $^{34}S$-$^{32}S$ and $^{36}S$-$^{32}S$ differences are 0.999387, 1.995796 and 3.99501 Da, respectively. Thus, the use to any non-$M_{mi}$ isotopes should cause the mass shift with ~1 Da as the basic unit. If the peak containing only $M_{mi}$ isotopes is considered as the original position, or position 0, the use of any smallest non-$M_{mi}$ isotope, e.g. $^{13}C$, $^{2}H$, $^{17}O$, $^{15}N$ and $^{33}S$, moves its isotopologue out of position 0 and to position 1. Likewise, the use of any second smallest non-$M_{mi}$ isotope, e.g. $^{18}O$ and $^{34}S$, should move its isotopologue from position 0 to position 2. In other words, the numbers and types of non-$M_{mi}$ isotopes in an isotopologue determine its position in the ion cluster. Given this principle, those isotopologues expected at the same cluster position can be identified, grouped and merged together to deduce their collective abundance in the mass spectrum.

Based on this concept, we can simply define the cluster position of isotopologues in an ion cluster. For each single-element isotopologue, its position number is equal to the result of the following equation:

$$\Sigma_{i=2}^{5}[(\Sigma_{i}N)\times(i-1)],$$

where $_iN$ is the number of the ith lightest isotope of the element included in the single-element isotopologue (see Table 1) and the i is the rounded integer of $(MM_I-MM_{MN})$ where $MM_I$ is the molecular mass of the isotope I and $MM_{MN}$ is the monoisotopic mass of the element.

Furthermore, for the molecule like protein with multiple elements, the position number of multi-element isotopologue is equal to the result of the following equation:

$$\Sigma_{i=2}^{5}[(\Sigma_{i}N_{e(j)}))\times(i-1)],$$

where $_iN_{e(j)}$ is the number of the ith lightest isotope of jth element, e(j), included in the multi-element isotopologue and the i is the rounded integer of $(MM_I-MM_{MN})$ where $MM_I$ is the molecular mass of the isotope I and $MM_{MN}$ is the monoisotopic mass of the element. The second (2nd) lightest isotopes, as i=2, are $^{13}C$, $^{2}H$, $^{15}N$, $^{17}O$, $^{33}S$; the third (3rd) lightest isotopes, as i=3, are $^{14}C$, $^{3}H$, $^{16}N$, $^{18}O$, $^{34}S$; the fourth (4th) lightest isotope, as i=4, is $^{35}S$; and the fifth (5th) lightest isotope, as i=5, is $^{36}S$ (see Table 1). Hence, isotopologues of a polypeptide with multiple elements can be grouped based on their position number in an ion cluster.

Figure 8:
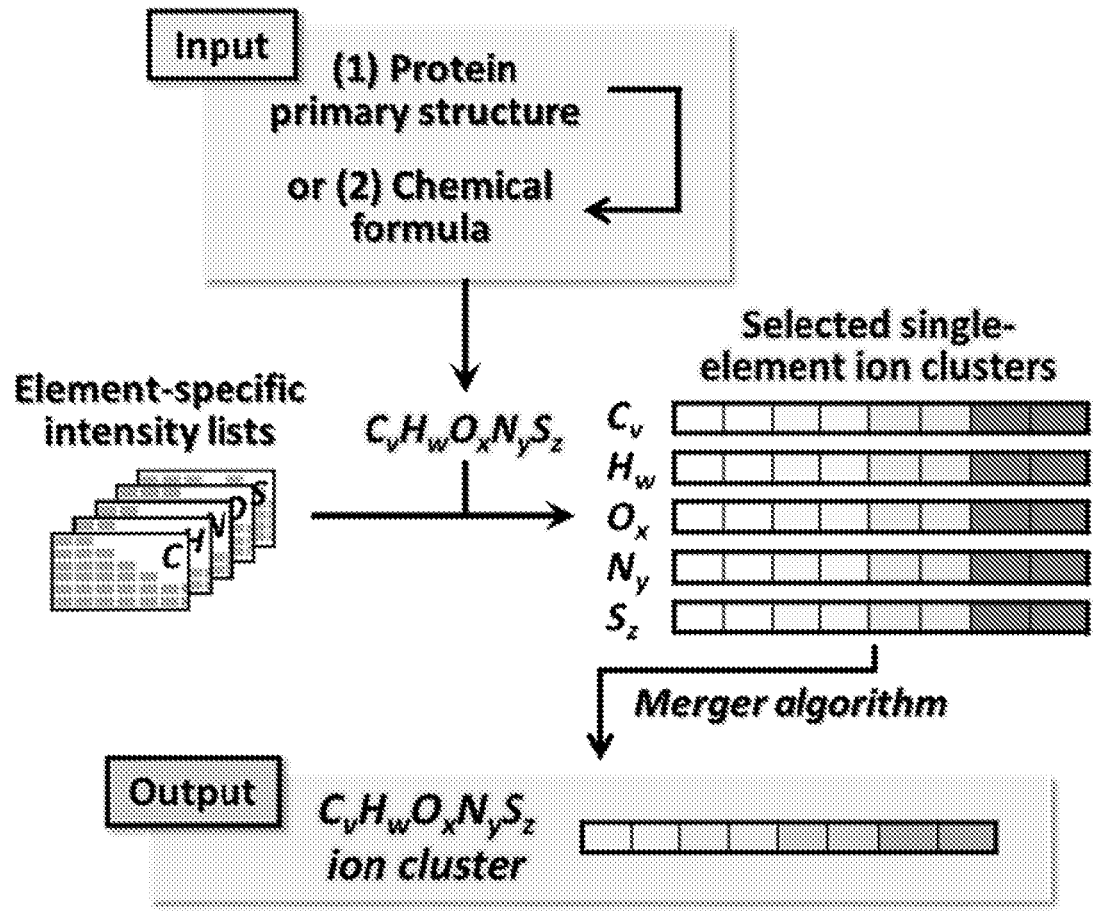
FIG. 8 illustrates that simulated isotope distribution can be computed by intensity list-based cluster deduction by MacroCluster.
Figure 9:
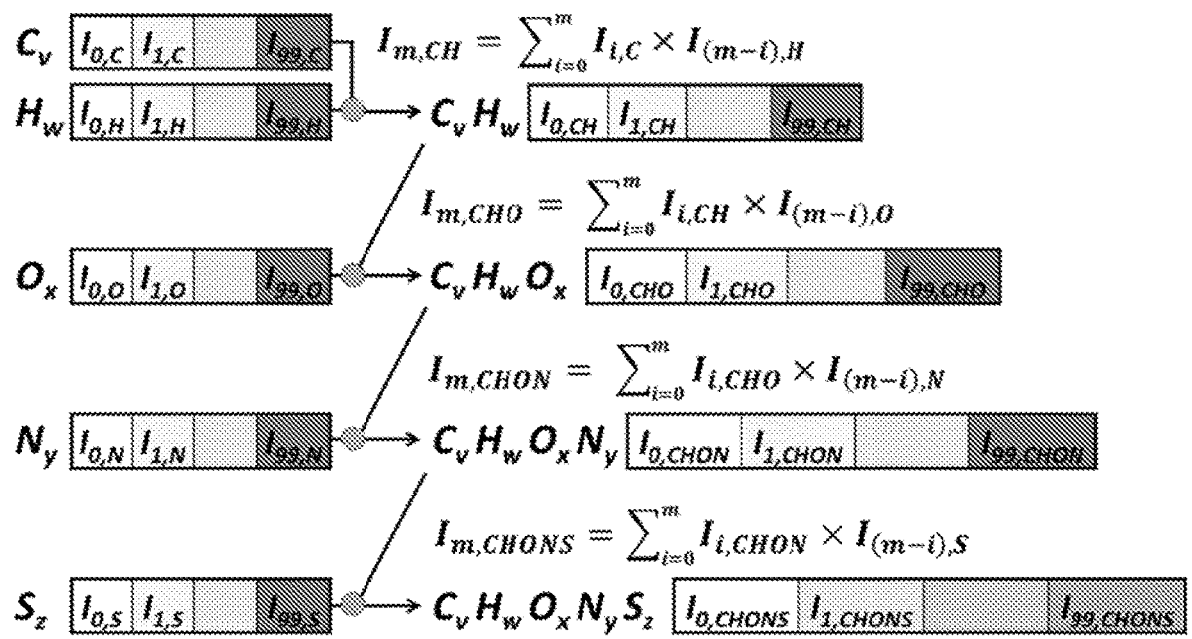
FIG. 9 illustrates the computation of simulated ion cluster based on gradually combining single-element ion clusters by Merger algorithm.

Macro Cluster program uses a stepwise process based on a group of ion clusters, each of which contains only one type of element but the same atom number of the analyzed molecule. For instance, if a protein has a chemical formula of $C_vH_wO_xN_yS_z$, the ion clusters of $C_v$, $H_w$, $O_x$, $N_y$, and $S_z$, which have been acquired using dynamic programming approach beforehand (see below), are fetched and then sequentially merged (FIG. 8). First, the $C_v$ ion cluster is merged with $H_w$ one. Based on the principle shown above, the new position of two merged peaks is equal to the sum of the two position numbers prior to their merging. Thus, the peak intensity $(I_{m,CH})$ of the m-th position of the resulted $C_vH_w$ cluster can be deduced according to the following:

$$I_{m,CH}=\Sigma_{i=0}^{m}I_{i,C}\times I_{(m-i),H}$$

where $I_{i,C}$, is the intensity of the peak at the i-th position of $C_v$ cluster and $I_{(m-i),H}$ is the intensity of the peak at the (m−i)-th position of the $H_w$ cluster. It is notable that, for the molecular mass range of most proteins, the intensities will be high enough for consideration only for the first few dozens of positions (data not shown). These observations help conclude that it is not necessary to perform a full calculation of all likely signals. Instead, we only carry out the merging of the first one hundred peaks in any clusters involved in the merging process. Once the peak intensities of $C_vH_w$ cluster is deduced, the following merging calculations continue (FIG. 9):

$$I_{m,CHO}=\Sigma_{i=0}I_{i,CH}\times I_{(m-i),O},$$

$$I_{m,CHON}=\Sigma_{i=0}^{m}I_{i,CHO}\times I_{(m-i),N}, \text{ and}$$

$$I_{m,CHONS}=\Sigma_{i=0}^{m}I_{i,CHON}\times I_{(m-i),S},$$

with the same merging principles mentioned above. Notably, only the peak intensities from 0- to 99-th positions are produced.

Intensity lists are preprocessed for rapid acquisition of needed information by Macro Cluster program As shown above, we need a series of ion clusters with only 1-Da mass difference used in integration analyses. It seems reasonable that the throughput in generation of these ion clusters can be drastically improved using pre-calculation concept. Hence, we decided to establish element-specific intensity lists, each of which contains the simulated ion clusters of imaginary compounds like $C_v$, $H_w$, $O_x$, $N_y$, and $S_z$. In order to generate such a list, we have tested binomial and polynomial extension methods (Yergey, *Int J Mass Spectrom Ion Phys* 52, 337-349 (1983); Yergey et al., *Anal Chem* 55, 353-356 (1983)), although a larger error may occur when the atom numbers increase beyond certain limits (data not shown). Rather, we developed a dynamic programming approach on the basis of the mentioned principle that inclusion of non-$M_{mi}$ isotopes causes corresponding positional shifts in ion clusters. For elements with two stable isotopes, e.g. carbon, there are two and only two types of 'pathways' to synthesize the isotopologues present in the n-th peak of the ion cluster $C_v$. The first way is to add $^{12}C$, the $M_{mi}$ isotope, to those isotopologues present at the same position (n) of the $C_{v-1}$ cluster; such a 'synthesis' does not produce positional shift. The other way is to add $^{13}C$, the only non-$M_{mi}$ carbon isotope, to those isotopologues present at the (n−1) position of the $C_{v-1}$ cluster. Since the smallest non-$M_{mi}$ isotope should cause a positional shift of 1, all of the products will be found at the n-th position of the $C_v$ cluster. Thus, the intensity $(I_{n,v})$ of in the n-th peak of the ion cluster $C_v$ should be equal to:

$$I_{n,v}=A_{12_C}\times I_{n,v-1}A_{13_C}\times I_{n-1,v-1},$$

where $A_{12_C}$ and $A_{13_C}$ are natural percentages of $^{12}C$ and $^{13}C$, and $I_{n,v-1}$ and $I_{n-1,v-1}$ are the peak intensities of the n- and (n−1)-th peaks in the $C_{v-1}$ cluster. Likewise, the intensity $(I_{n,v})$ of in the n-th peak of the ion clusters $H_w$ and $N_y$ is supposed to correspond to:

$$I_{n,w}=A_{1_H}\times I_{n,w-1}+A_{2_H}\times I_{n-1,w-1}, \text{ and}$$

$$I_{n,v}=A_{14_N}\times I_{n,y-1}+A_{15_N}\times I_{n-1,y-1}, \text{ respectively (FIG. 10).}$$

This means that the ion cluster of each element-specific compound with a specific atom number can always be deduced by the cluster of its derivative with one atom subtracted. This principle can be further extended to the calculation of $O_x$ and $S_z$ clusters. For the former, there exist two non-$M_{mi}$ isotopes, $^{17}O$ and $^{18}O$, whose inclusion should lead to one and two steps in positional shift, respectively. Thus, the intensity $(I_{n,x})$ of in the n-th peak of the ion cluster $O_x$ should be equal to:

$$I_{n,x}=A_{16_O}\times I_{n,x-1}+A_{17_O}\times I_{n-1,x-1}+A_{18_O}\times I_{n-2,x-1},$$

where $A_{16_O}$, $A_{17_O}$ and $A_{18_O}$ are natural percentages of $^{16}O$, $^{17}O$ and $^{18}C$, and $I_{n,x-}$, $I_{n-1,x-1}$ and $I_{n-2,x-1}$ are the peak intensities of the n-, (n−1)- and (n−2)-th peaks in the $O_{x-1}$ cluster (FIG. 11). When $S_z$ clusters are made, there are three non-$M_{mi}$ isotopes, namely $^{33}S$, $^{34}S$ and $^{36}S$, for consideration. The intensity $(I_{n,z})$ of in the n-th peak of the ion cluster $S_z$ should be equal to:

$$I_{n,z}=A_{32_S}\times I_{n,z-1}+A_{33_S}\times I_{n-1,z-1}+A_{34_S}\times I_{n-2,z-1}+A_{36_S}\times I_{n-4,z-1},$$

where $A_{32_S}$, $A_{33_S}$, $A_{34_S}$ and $A_{36_S}$ are natural percentages of $^{32}S$, $^{33}S$, $^{34}S$ and $^{36}S$, and $I_{n,z-1}$, $I_{n-1,z-1}$, $I_{n-2,z-1}$ and $I_{n-4,z-1}$ are the peak intensities of the n-, (n−1)-, (n−2)- and (n−4)-th peaks in the $S_{z-1}$ cluster (FIG. 12). With these equations, we have generated the intensity lists for these five elements using computer programming (see FIGS. 19-23).

Example 15. Primary Structure Verification of De-N-Glycosylated Eprex Using CompareMS Program To verify the chemical formula of the examined therapeutic, de-N-glycosylated Eprex with an O-linked trisaccharide, the observed master ion cluster (solid-lined profile) was first obtained by MS analysis followed by informatics-based processing of IntegrateMS (FIG. 13A). Meanwhile, the sequence of this construct was accessed for MacroCluster. Simulated ion cluster of the putative therapeutic was established (dash-lined profile with m as zero) and a series of predicted ion clusters of the putative chemical formulas with added or removed several hydrogen atoms were also constructed (dash-lined profile). The numbers at the top of bars in the lower graph are the difference scores (DS) for these derivatives. The CompareMS result of de-N-glycosylated Eprex with an O-linked tetrasaccharide (FIG. 13B). Lot number of Eprex: EFS5600.

Example 16. Primary Structure Verification of De-N-Glycosylated Recormon Using CompareMS Program To verify the chemical formula of the examined therapeutic, de-N-glycosylated Recormon with an O-linked trisaccharide, the observed master ion cluster (solid-lined profile) was first obtained by MS analysis followed by informatics-based processing of IntegrateMS (FIG. 14A). Meanwhile, the sequence of this construct was accessed for MacroCluster. Simulated ion cluster of the putative therapeutic was established (dash-lined profile with m as zero) and a series of predicted ion clusters of the putative chemical formulas with added or removed several hydrogen atoms were also constructed (dash-lined profile). The numbers at the top of bars in the lower graph are the difference scores (DS) for these derivatives. The CompareMS result of de-N-glycosylated Recormon with an O-linked tetrasaccharide (FIG. 14B). Lot number of Recormon: H0743H01.

Example 17. CompareMS Program Finds the Match of Master Ion Cluster from a Series of Ion Clusters Produced by MacroCluster In order to validate the chemical formula of the protein analyte, CompareMS has been coded to employ MacroCluster to produce ion clusters for a series of compounds with exact one H atom difference.

Routinely, three compounds with extra H atoms are produced, i.e. one to three H atoms are added to the chemical formula of the protein analyte. Also, three compounds with H atoms subtracted, i.e. one to three atoms are removed from the original chemical formula. The ion clusters of a total of seven compounds are then produced. In order to quantify the difference between master ion cluster and each of seven ion clusters, CompareMS tags a parameter, or difference score (DS), to each ion cluster. The difference score is defined as:

$$X^2 = \sum_{k=0}^{n} \frac{(A_{o,k} - E_{o,k})^2}{E_{o,k}} + \sum_{k=0}^{n} \frac{(A_{t,k} - E_{t,k})^2}{E_{t,k}},$$

where $A_{o,k}$ and $A_{t,k}$ represent the relative abundances of k-th peaks in the observed and simulated clusters, while $E_{o,k}$ and $E_{t,k}$ represent the expected abundances of k-th peaks, respectively. A smaller DS means higher similarity between the two ion clusters. Among all the examined clusters, the one with smallest DS is marked and we examine whether its chemical formula is consistent with the listed protein primary structure. If the answer is positive, the preliminary validation of protein primary structure is completed (FIG. 1).

Figure 13:
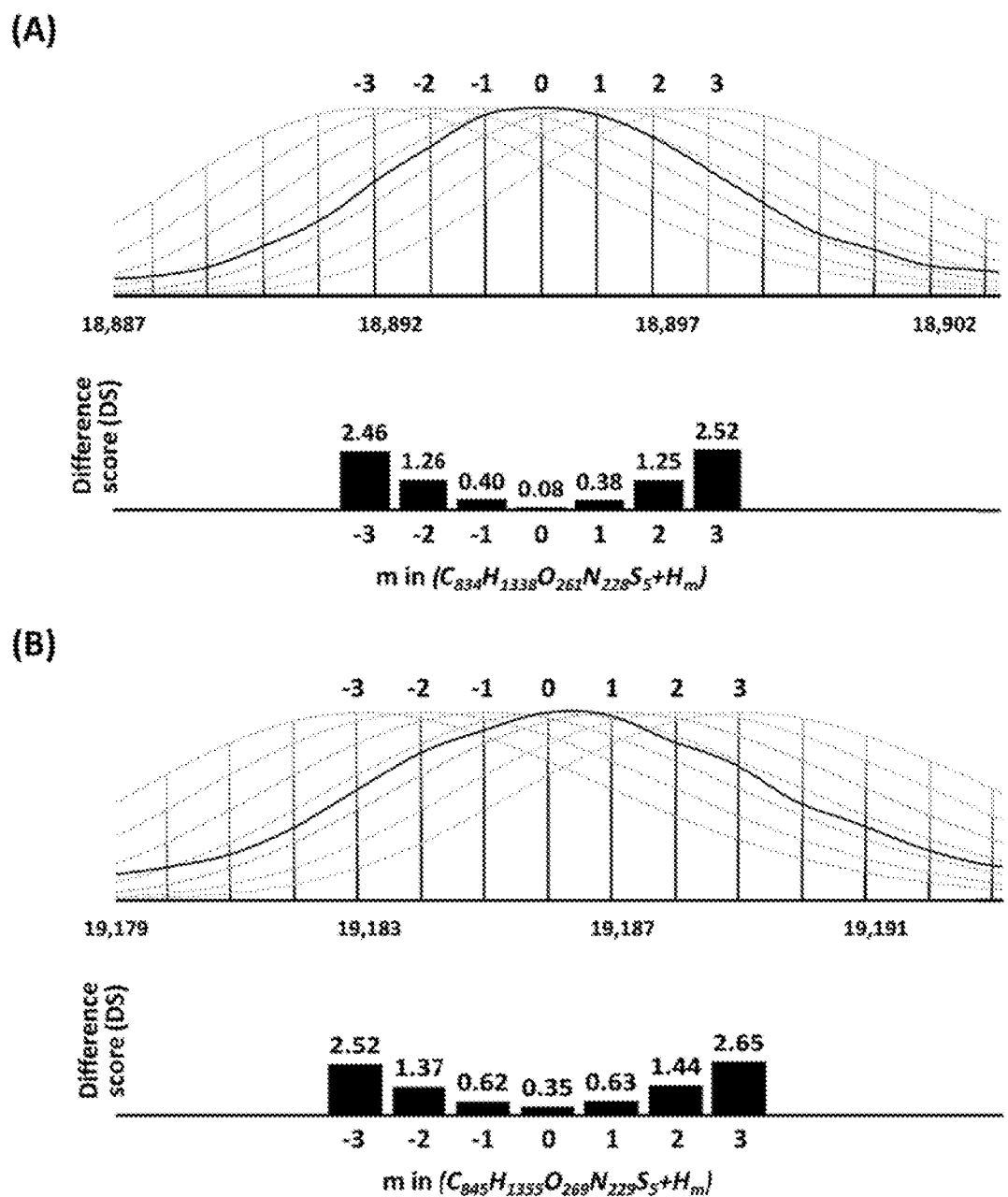
FIG. 13 illustrates the primary structure verification of de-N-glycosylated Eprex using CompareMS program.

Example 18. The Primary Structures of De-N-Glycosylated Erythropoietins are Validated Using CompareMS Program Primary structure of erythropoietin with the removal of N-linked glycans is said to contain 165 amino acid sequence with three asparagines replaced as three aspartic acids, one O-linked glycosylation and two disulfide bonds. Among these modifications, O-linked glycosylation is expressed as the addition of either one trisaccharide or one tetrasaccharide (FIG. 2). As mentioned above, we have produced the master ion clusters for de-N-glycosylated erythropoietins with an O-linked trisaccharide and with an O-linked tetrasaccharide, respectively. We then use their chemical formulas to produce respective series of simulated ion clusters. For de-N-glycosylated erythropoietin with an O-linked trisaccharide analyses, we used $C_{834}H_{1338}O_{261}N_{228}S_5$ to produce the seven ion clusters, and difference scores (DS) were assigned to each of these clusters. We found that, regardless of Eprex or Recormon, the structure without H added or removed has the lowest difference score, i.e. (0.08 for Eprex or 0.01 for Recormon). As the structures with one H removed and one H added have very similar difference scores (FIGS. 13 and 14), these data suggest that the majority of the de-N-glycosylated erythropoietin with two disulfide bonds and bearing an O-linked trisaccharide has its chemical formula as $C_{834}H_{1338}O_{261}N_{228}S_5$. Indeed, our analyses successfully validate the primary structure of de-N-glycosylated erythropoietin. For de-N-glycosylated erythropoietin with an O-linked tetrasaccharide analyses, we used $C_{845}H_{1355}O_{269}N_{229}S_5$ to produce the simulated ion clusters, and difference scores were calculated. We also found the structures without H added or removed have the lowest difference score for two erythropoietin with different brands (i.e. 0.35 for Eprex and 0.1 for Recormon). The two structures with one extra H and fewer H had similar difference scores (FIGS. 13 and 14). Hence, we conclude that the chemical of the de-N-glycosylated erythropoietin with an O-linked tetrasaccharide should be as $C_{845}H_{1355}O_{269}N_{229}S_5$, which also validates the listed primary structure.

To evaluate the content of erythropoietin products with different brands, Eprex and Recormon are analyzed in triplicate through our intact protein analyses.

Triplicate experiments of different branded erythropoietin samples were performed through our informatics-based procedures for assurance of method repeatability. The abundance of de-N-glycosylated erythropoietins with an O-linked trisaccharide or an O-linked tetrasaccharide were respectively recorded and compared in different runs. The mean ratio of a trisaccharide-containing Eprex versus a tetrasaccharide-containing one in triplicate is 1.21±0.19 while the Recormon one is 0.63±0.04 (Table 2). These results got low standard deviations which first shows the reproducibility of our analytical methods. Furthermore, our platform reveals different ratios of O-linked oligosaccharide content present in two different branded erythropoietin products. This indicates that our methods can not only qualitatively verify the primary structure of proteins, but also can quantitatively demonstrate the modification ratios on intact protein structure. This utility can be further applied for quality control of protein therapeutics such as detection of lot-to-lot variations, or even similarity of various branded protein products.

TABLE 2

The ratios of trisaccharide-modified to tetrasaccharide-modified erythropoietins from Eprex and Recormon.

| Protein (#lot) | No. | No. of sugars | Abundance | Tri/Tetra | Mean (±S.D.) |
|---|---|---|---|---|---|
| Eprex ® (#EFS5600) | 1. | Tri | 1.55E+04 | 1.00 | 1.21 (±0.19) |
| | | Tetra | 1.56E+04 | | |
| | 2. | Tri | 3.05E+04 | 1.38 | |
| | | Tetra | 2.21E+04 | | |
| | 3. | Tri | 2.92E+04 | 1.26 | |
| | | Tetra | 2.32E+04 | | |
| Recormon ® (#H0743H01) | 1. | Tri | 4.62E+04 | 0.66 | 0.63 (±0.04) |
| | | Tetra | 6.96E+04 | | |
| | 2. | Tri | 5.00E+04 | 0.63 | |
| | | Tetra | 7.88E+04 | | |
| | 3. | Tri | 5.46E+04 | 0.59 | |
| | | Tetra | 9.23E+05 | | |

Example 19. Protein Sequence of the Tested Therapeutic, Humulin R

Primary structure information of Humulin R is provided to build up the baseline for establishment of simulated ion clusters. The putative therapeutic, Humulin R, is supposed to contain A and B polypeptide chains and three disulfide linkages (FIG. 15, solid lines), which results in its putative chemical formula as $C_{257}H_{383}O_{77}N_{65}S_6$. Throughout our protein analyte verification study, we verified the proposed protein primary structure.

Figures 15, 16:
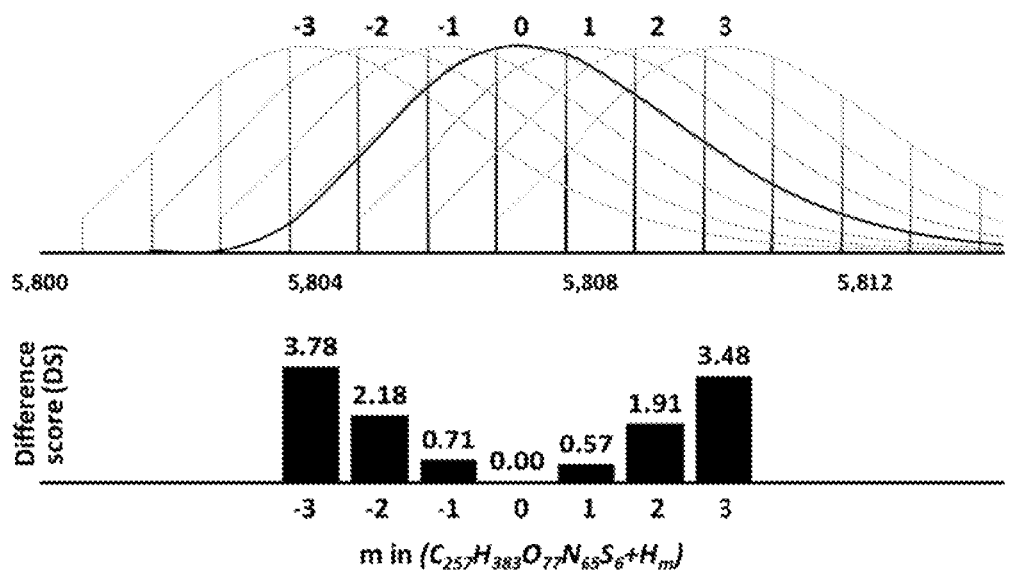
FIG. 15 shows protein sequence of the tested therapeutic, Humulin R.
FIG. 16 illustrates the primary structure verification of protein therapeutic, Humulin R.

Example 20. Primary Structure Verification of Protein Therapeutic, Humulin R, Using the Present Invention To verify the chemical formula of the examined therapeutic, Humulin R, the observed master ion cluster (FIG. 16, solid-lined profile) was first obtained by MS analysis followed by informatics-based processing using IntegrateMS. Meanwhile, the sequence of this construct was accessed for Macro Cluster. Simulated ion cluster of the putative therapeutic was established (FIG. 16, dash-lined profile with m as zero) and a series of predicted ion clusters of the putative chemical formulas with added or removed several hydrogen atoms were also constructed (FIG. 16, dash-lined profile). The numbers at the top of bars in the lower graph are the difference scores (DS) for these derivatives. Lot number of Humulin R: A930615.

Example 21. Protein Sequence of the Tested Therapeutic, Saizen

Primary structure information of Saizen is provided to build up the baseline for establishment of simulated ion clusters. The putative therapeutic, Saizen, is supposed to contain 191 amino acids and two disulfide linkages (FIG. 17, solid lines), which results in its putative chemical formula as $C_{990}H_{1528}O_{300}N_{262}S_7$. Throughout our protein analyte verification study, we verified the proposed protein primary structure.

Example 22. Primary Structure Verification of Protein Therapeutic, Saizen

Figures 17, 18:
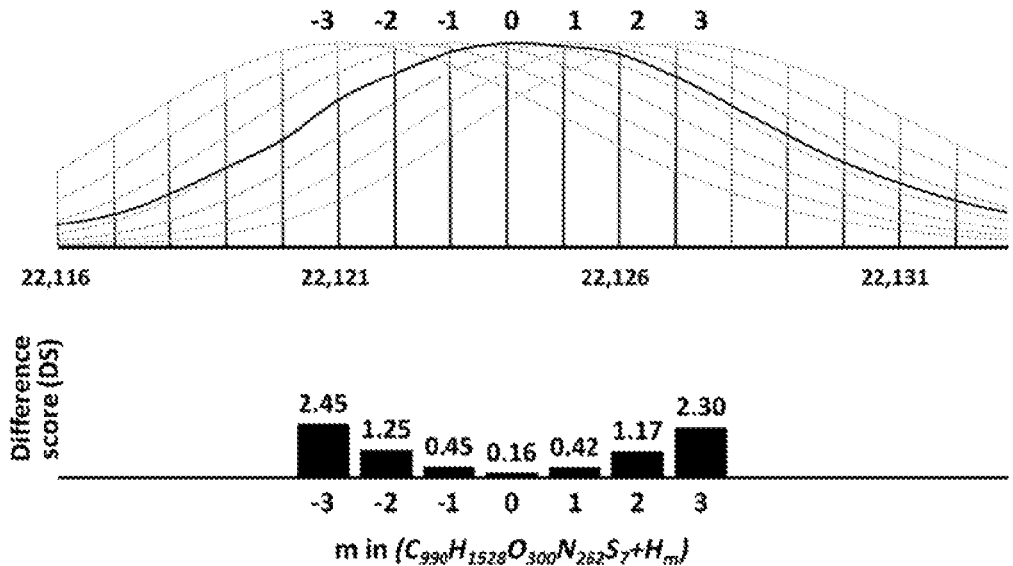
FIG. 17 shows the protein sequence of the tested therapeutic, Saizen.
FIG. 18 illustrates the primary structure verification of protein therapeutic, Saizen.

To verify the chemical formula of the examined therapeutic, Saizen, the observed master ion cluster (FIG. 18, solid-lined profile) was first obtained by MS analysis followed by informatics-based processing using IntegrateMS. Meanwhile, the sequence of this construct was accessed for MacroCluster. Simulated ion cluster of the putative therapeutic was established (FIG. 18, dash-lined profile with m as zero) and a series of predicted ion clusters of the putative chemical formulas with added or removed several hydrogen atoms were also constructed (FIG. 18, dash-lined profile). The numbers at the top of bars in the lower graph are the difference scores (DS) for these derivatives. Lot number of Saizen: BA020963.

Example 23. Applications of Our Methods on Quality Control of Various Protein Therapeutics Verification of protein primary structure is the important step for quality control of protein therapeutics after production from a biological system. Different brands of erythropoietins are primarily used as examples for the test drive of our achievement on verification of protein primary structure. For magnifying application of this method, we then test other protein drugs, such as humulin R and Saizen with our approaches. Humulin is similar to the insulin the body makes naturally, which indicates as an adjunct to diet and exercise to improve glycemic control in adults and children with type 1 and type 2 diabetes mellitus. For humulin R analyses, chemical formula of $C_{257}H_{383}O_{77}N_{65}S_6$ was used to produce simulated ion clusters and the structure without H added or removed has the lowest difference score, i.e. (0.00) (FIGS. 15 and 16). This successfully validates the primary structure of humulin R with three disulfide bonds. Saizen is a prescription medicine indicated for the treatment of growth hormone deficiency (GHD) in children and adults. The Saizen structure used in treatment is identical to the growth hormone produced by the pituitary gland. For Saizen analyses, we used $C_{990}H_{1528}O_{300}N_{262}S_7$ to produce the simulated ion clusters, and difference scores were calculated. The structure without H added or removed was found to have the lowest difference score for Saizen i.e. (0.16), which is consistent with the listed primary structure of Saizen with two disulfide bonds (FIGS. 17 and 18).

In summary, we have developed a series of computer programs that can be used to evaluate whether the chemical formula determined by high-resolution mass spectrometry is consistent with its protein primary structure. Since such evaluation is rapid, effective and consistent, this method can be applied to quality control of protein therapeutics.

What is claimed is:

1. A method for verifying the primary structure of a protein comprising:
    obtaining a mass spectrum of a full-length protein;
    identifying from the mass spectrum a plurality of ion clusters with a mass corresponding to the full-length protein but with different charge states;
    calculating a master ion cluster from the plurality of ion clusters; and
    comparing the master ion cluster with a series of simulated ion clusters generated based on the chemical formula of the full-length protein with or without a modification, to find a best fitted simulated ion cluster;
    wherein the master ion cluster is calculated by a process comprising: summing up the intensities of the most abundant peak at $(m/z)_{ma}$ of each of the plurality of ion clusters, to obtain a starting summation; summing up the intensities of the next larger isotopic peak p(+1), with an m/z larger than the $(m/z)_{ma}$ according to an average isotope spacing, of each most abundant peak, to obtain a first right summation;

and summing up the intensities of the next smaller isotopic peak p(−1), with an m/z smaller than the (m/z)$_{ma}$ according to the average isotope spacing, of each most abundant peak, to obtain a first left summation.

2. The method of claim 1, wherein a plurality of right summations of a respective plurality of isotopic peaks p(+l) are obtained, a plurality of left summations of a respective plurality of isotopic peaks p(−m) are obtained, and the starting summation, the plurality of left summations and the plurality of right summations are normalized by dividing by the largest summation among all the summations, wherein l and m each is a positive integer, the isotopic peak p(+l) is the next larger isotopic peak relative to the isotopic peak p(+(l−1)) according the average isotope spacing, and the isotopic peak p(−m) is the next smaller isotopic peak relative to the isotopic peak p(−(m−1)) according the average isotope spacing.

3. The method of claim 1, wherein each of the intensities is normalized by dividing by the charge state of the corresponding isotopic peak before being summed up.

4. The method of claim 1, wherein the average isotope spacing is about 1 Dalton.

5. The method of claim 4, wherein the average isotope spacing is 1.00235 Dalton.

6. The method of claim 1, wherein the mass spectrum is obtained through a high-resolution mass spectrometry.

7. The method of claim 1, wherein the master ion cluster and the series of simulated ion clusters are compared by a method selected from the group consisting of chi-square test, Pearson's chi-square test, chi-square test with Yate's correlation, Fisher's exact test, McNemar's test, and Cochran's Q test.

8. The method of claim 1, wherein each of the series of simulated ion clusters is generated by a process comprising: given a chemical formula $C_vH_wO_xN_yS_z$ of the full-length protein with or without a modification, combining putative ion clusters of $C_v$, $H_w$, $O_x$, $N_y$, and $S_z$ to obtained the simulated ion cluster of the full-length protein with or without the modification, wherein the putative ion cluster of $C_v$ is represented by the intensities $I_{n,v}=A_{12_C} \cdot I_{n,v-1}+A_{13_C} \cdot I_{n-1,v-1}$, $A_{12_C}$ and $A_{13_C}$ being the natural abundances of $^{12}C$ and $^{13}C$ respectively, for the n-th putative isotopic peak starting from the 0-th peak being the putative monoisotopic peak; the putative ion cluster of $H_w$ is represented by the intensities $I_{n,w}=A_{1_H} \cdot I_{n,w-1}+A_{2_H} \cdot I_{n-1,w-1}$, $A_{1_H}$ and $A_{2_H}$ being the natural abundances of $^1H$ and $^2H$ respectively, for the n-th putative isotopic peak starting from the 0-th peak being the putative monoisotopic peak; the putative ion cluster of $S_z$ is represented by the intensities $I_{n,z}=A_{16_O} \cdot I_{n,x-1}+A_{17_O} \cdot I_{n-1,x-1}+A_{18_O}$, $A_{17_O}$ and $A_{18_O}$ being the natural abundances of $^{16}O$, $^{17}O$ and $^{18}O$ respectively, for the n-th putative isotopic peak starting from the 0-th peak being the putative monoisotopic peak; the putative ion cluster of $N_y$ is represented by the intensities $I_{n,y}=A_{14_N} \cdot I_{n,y-1}+A_{15_N} \cdot I_{n-1,y-1}$, $A_{14_N}$ and $A_{15_N}$ being the natural abundances of $^{14}N$ and $^{15}N$ respectively, for the n-th putative isotopic peak starting from the 0-th peak being the putative monoisotopic peak; and the putative ion cluster of $S_z$ is represented by the intensities $I_{n,z}=A_{32_S} \cdot I_{n,z-1}+A_{33_S} \cdot I_{n-1,z-1}+A_{34_S} \cdot I_{n-2,z-1}+A_{36_S} \cdot I_{n-4,z-1}$, $A_{32_S}$, $A_{33_S}$, $A_{34_S}$ and $A_{36_S}$ being the natural abundances of $^{32}S$, $^{33}S$, $^{34}S$ and $^{36}S$ respectively, for the n-th putative isotopic peak starting from the 0-th peak being the putative monoisotopic peak.

9. The method of claim 8, wherein the putative ion clusters of $C_v$, $H_w$, $O_x$, $N_y$, and $S_z$ are combined one by one.

10. The method of claim 8, wherein the putative ion clusters of $C_v$, $H_w$, $O_x$, $N_y$, and $S_z$ are combined according to the positions of the peaks.

11. The method of claim 9, wherein the putative ion clusters of $C_v$, $H_w$, $O_x$, $N_y$, and $S_z$ are combined by a process comprising: (i) calculating the intensities $I_{M,CH}$, each of which equals to $\Sigma_{i=0}^{M} I_{i,v} \times I_{(M-i),w}$; (ii) calculating the intensities $I_{m,cHo}$, each of which equals to $\Sigma_{i=0}^{M} I_{i,CH} \times I_{(M-i),x}$; (iii) calculating the intensities $I_{M,CHON}$, each of which equals to $\Sigma_{i=0}^{M} I_{i,CHO} \times I_{(M-i),y}$; (iv) calculating the intensities $I_{M,CHONS}$, each of which equals to $\Sigma_{i=0}^{M} I_{i,CHON} \times I_{(M-i),z}$; wherein i is a non-negative integer and M is the number of putative isotopic peaks other than the putative monoisotopic peak; and wherein the intensities $I_{M,CHONS}$ represents a simulated ion cluster of the full-length protein with or without the modification.

12. A method according to claim 1, wherein the said series of simulated ion clusters correspond to the series of the chemical formulas that are produced by adding or removing several hydrogen atoms from the chemical formula of the said protein sample.

13. A method according to claim 12, wherein said series of simulated ion clusters comprising ion clusters, each of which is computationally generated by combination of multiple single-element ion clusters, each of which has the number of atoms the same as that of chemical formula of the said ion cluster member.

14. A method according to claim 13, wherein each of said ion clusters results from the sequential pairwise combinations of single-element ion clusters based on the principle that isotopologues with the same position number in the said ion cluster member are integrated together in terms of the percentages in the ion cluster and weighted molecular masses.

15. A method according to claim 14, wherein said integration of percentages of isotopologues in the ion cluster is the summation of all percentages of all isotopologues with the same position number.

16. A method according to claim 14, wherein said molecular masse are the result of the equation:

$$(MM_1 \times P_1 + MM_2 \times P_2)/(P_1+P_2)$$

where $MM_1$ and $MM_2$ are the molecular masses and $P_1$ and $P_2$ are the percentages of isotopologues in the first and second ion clusters, respectively, before integration.

17. A method according to claim 7, wherein the i is the rounded integer of $(MM_I-MM_{MN})$ where $MM_I$ is the molecular mass of the said isotope I and $MM_{MN}$ is the monoisotopic mass of the said element.

18. A method according to claim 7, wherein the second (2nd) lightest isotopes, as i=2, are $^{13}C$, $^2H$, $^{15}N$, $^{17}O$, $^{33}S$; the third (3rd) lightest isotopes, as i=3, are $^{14}C$, $^3H$, $^{16}N$, $^{18}O$, $^{34}S$; the fourth (4th) lightest isotope, as i=4, is $^{35}S$; and the fifth (5th) lightest isotope, as i=5, is $^{36}S$.

19. A method according to claim 13, wherein the production of each single-element ion cluster is accomplished based on the principle that isotopologues with same position number in the said single-element ion cluster are integrated together in terms of the percentages in the ion cluster and weighted molecular masses.

20. A method according to claim 19, wherein the position number of each single-element isotopologue is equal to the result of the following equation:

$$\Sigma_{i=2}^{5}[(\Sigma_i N) \times (i-1)]$$

where $_iN$ is the number of the ith lightest isotope of the said element included in the said single-element isotopologue.

21. A method according to claim 20, wherein the i is the rounded integer of $(MM_I-MM_{MN})$ where $MM_I$ is the molecular mass of the said isotope I and $MM_{MN}$ is the monoisotopic mass of the said element.

22. A method according to claim 13, wherein each of the said single-element ion clusters is directly taken from the databases consisting the simulated ion clusters for single-element compounds containing different numbers of atoms.

* * * * *